(12) United States Patent
Bukhovko et al.

(10) Patent No.: US 10,780,421 B2
(45) Date of Patent: Sep. 22, 2020

(54) AEROSOL PROCESSING METHOD FOR CONTROLLED COATING OF SURFACE SPECIES TO GENERATE CATALYSTS

(71) Applicant: Saudi Arabian Oil Company, Dhahran (SA)

(72) Inventors: Maxim Bukhovko, Boston, MA (US); Michele Louisa Ostraat, Somerville, MA (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/998,699

(22) Filed: Aug. 16, 2018

(65) Prior Publication Data

US 2019/0054449 A1 Feb. 21, 2019

Related U.S. Application Data

(60) Provisional application No. 62/546,765, filed on Aug. 17, 2017.

(51) Int. Cl.
*B01J 23/30* (2006.01)
*B01J 37/00* (2006.01)
(Continued)

(52) U.S. Cl.
CPC ............. *B01J 23/30* (2013.01); *B01J 21/08* (2013.01); *B01J 21/12* (2013.01); *B01J 23/24* (2013.01);
(Continued)

(58) Field of Classification Search
CPC ... B01J 23/30; B01J 21/08; B01J 21/12; B01J 23/24; B01J 23/32; B01J 23/38;
(Continued)

(56) References Cited

U.S. PATENT DOCUMENTS 3,645,684 A 2/1972 De Cuir
3,865,751 A 2/1975 Banks et al.
(Continued)

FOREIGN PATENT DOCUMENTS

EP 276096 A1 7/1988
WO 2005016823 A1 2/2005
(Continued)

OTHER PUBLICATIONS

Garcia et al (Multifaceted tungsten oxide films grown by thermal evaporation, Surf Coat Tech, 283(2015) 177-183). (Year: 2015).*
(Continued)

*Primary Examiner* — Patricia L. Hailey
*Assistant Examiner* — Michael Forrest
(74) *Attorney, Agent, or Firm* — Dinsmore and Shohl, LLP

(57) ABSTRACT

A method of producing a catalyst comprises generating an aerosolized flow of catalyst support particles, heating a catalytically active compound precursor to produce a catalytically active compound precursor vapor, contacting the aerosolized flow of catalyst support particles with the catalytically active compound precursor vapor, and condensing the catalytically active compound precursor onto the catalyst support particles to produce the catalyst comprising catalytically active compound deposited on surfaces of the catalyst support particles. The method may further comprise aerosolizing a catalyst support precursor mixture, drying the aerosolized catalyst support precursor mixture in a first heating zone to form an aerosolized flow of catalyst support particles, and contacting the catalyst support particles with a catalytically active compound precursor vapor in a second heating zone to form the catalyst comprising the layer of the catalytically active compound deposited on surfaces of the catalyst of catalyst support particles.

12 Claims, 8 Drawing Sheets

(51) Int. Cl.

| | |
|---|---|
| *B01J 23/32* | (2006.01) |
| *B01J 35/00* | (2006.01) |
| *B01J 23/38* | (2006.01) |
| *B01J 23/24* | (2006.01) |
| *B01J 37/08* | (2006.01) |
| *B01J 37/02* | (2006.01) |
| *B01J 21/08* | (2006.01) |
| *B01J 21/12* | (2006.01) |
| *B01J 35/02* | (2006.01) |
| *C07C 6/04* | (2006.01) |

(52) U.S. Cl.
CPC ............... *B01J 23/32* (2013.01); *B01J 23/38* (2013.01); *B01J 35/006* (2013.01); *B01J 35/008* (2013.01); *B01J 35/026* (2013.01); *B01J 37/0054* (2013.01); *B01J 37/0217* (2013.01); *B01J 37/0221* (2013.01); *B01J 37/0232* (2013.01); *B01J 37/08* (2013.01); *C07C 6/04* (2013.01); *C07C 2521/08* (2013.01); *C07C 2523/30* (2013.01)

(58) Field of Classification Search
CPC ...... B01J 35/006; B01J 35/008; B01J 35/026; B01J 37/0054; B01J 37/0217; B01J 37/0221; B01J 37/0232; B01J 37/08; C07C 6/04

See application file for complete search history.

(56) References Cited

U.S. PATENT DOCUMENTS

| | | | |
|---|---|---|---|
| 3,928,177 A | 12/1975 | Hayes | |
| 4,575,575 A | 3/1986 | Drake et al. | |
| 4,684,760 A | 8/1987 | Drake | |
| 5,204,088 A | 4/1993 | Noebel et al. | |
| 5,230,789 A * | 7/1993 | Chao ................ | B01J 27/182 208/111.3 |
| 5,304,692 A | 4/1994 | Yamada et al. | |
| 5,340,560 A | 8/1994 | Rohr et al. | |
| 6,551,567 B2 | 4/2003 | Konya et al. | |
| 6,586,785 B2 | 7/2003 | Flagan et al. | |
| 6,723,606 B2 | 4/2004 | Flagan et al. | |
| 6,780,805 B2 | 8/2004 | Faber et al. | |
| 8,097,555 B2 | 1/2012 | Costa et al. | |
| 8,246,933 B2 | 8/2012 | Jiang et al. | |
| 8,415,267 B2 | 4/2013 | Lee | |
| 8,440,874 B2 | 5/2013 | Ramachandran et al. | |
| 8,895,795 B2 | 11/2014 | Krawczyk et al. | |
| 9,586,198 B2 | 3/2017 | Park et al. | |
| 9,682,367 B2 | 6/2017 | Ali et al. | |
| 9,969,621 B2 | 5/2018 | Ostraat | |
| 2002/0035950 A1 | 3/2002 | Mangold et al. | |
| 2002/0177311 A1 | 11/2002 | Schumacher et al. | |
| 2004/0101454 A1* | 5/2004 | Johnson ................ | B01J 6/007 422/199 |
| 2005/0118096 A1 | 6/2005 | Robson et al. | |
| 2008/0011876 A1 | 1/2008 | Ostraat | |
| 2010/0056839 A1 | 3/2010 | Ramachandran et al. | |
| 2010/0286432 A1 | 11/2010 | Tateno et al. | |
| 2010/0286458 A1* | 11/2010 | Iselborn ................ | C07C 5/2512 585/253 |
| 2011/0077444 A1 | 3/2011 | Butler | |
| 2011/0092757 A1 | 4/2011 | Akagishi et al. | |
| 2012/0016172 A1 | 1/2012 | Miyazoe et al. | |
| 2012/0039782 A1 | 2/2012 | Nicholas | |
| 2014/0027346 A1 | 1/2014 | Chaumonnot et al. | |
| 2017/0001925 A1 | 1/2017 | Abudawoud et al. | |
| 2017/0136445 A1 | 5/2017 | Ostraat et al. | |
| 2017/0320747 A1 | 11/2017 | Ostraat | |

FOREIGN PATENT DOCUMENTS

| | | |
|---|---|---|
| WO | 2016061262 A1 | 4/2016 |
| WO | 2016068814 A1 | 5/2016 |
| WO | 2017083162 A1 | 5/2017 |
| WO | 2018136576 A1 | 7/2018 |

OTHER PUBLICATIONS

Silverman et al (Methods of Generating Solid Aerosols, J Air Pollution Control Assoc., 6:2, (1956), 76-83). (Year: 1956).*

Bhuiyan et al., "Kinetics Modelling of 2-Butene Metathesis over Tungsten Oxide Containing Mesoporous Silica Catalyst", The Canadian Journal of Chemical Engineering, 2014, 92, 1271-1282, Canadian Society for Chemical Engineering.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 467, 224-234, Elsevier.

Bukhovko et al., "Continuous Aerosol Flow Reactors for the Controlled Synthesis of heterogeneous Catalyst Particles", AIChE Annual Meeting, Nov. 8-13, 2015.

Debecker et al., "A Non-Hydrolytic Sol-Gel Route to Highly Active MoO2—SiO2—Al2O3 metathesis Catalysts", Catalysis Science & Technology, 2012, 2:6, 1075-1294, RSC Publishing.

Debecker et al., "Aerosol Route to Nanostructured WO3—SiO2—Al2O3 Metathesis Catalysts: Toward Higher Propene Yield", Applied Catalysis A: General, 2014, 470, 458-466, Elsevier.

Debecker et al., "Flame-Made MoO3/SiO2—Al2o3 Metathesis Catalysts with highly Dispersed and Highly Active *Molybdate* Species", Journal of Catalysis, 2011, 277, 154-163, Elsevier.

Hyeon-Lee et al., "Fractal Analysis of Flame-Synthesized Nanostructured Silica and Titania Powders Using Small-Angle X-Ray Scattering", Langmuir 1998, 5751-5756, 14, American Chemical Society.

International Search Report and Written Opinion for serial No. PCT/US2017/030014, dated Jul. 11, 2017.

International Search Report and Written Opinion pertaining to PCT/US2016/060258 dated Mar. 7, 2017.

Ishihara et al., "Hydrocracking of 1-methylnaphthalene/decahydronaphthalene mixture catalyzed by zeolite-alumina composite supported NiMo catalysts", Fuel Processing Technology 116, pp. 222-227, 2013.

Keskinen et al., "On-Line Characterization of Morphology and Water Adsorption on Fumed Silica Nanoparticles", Aerosol Science and Technology, 2011, 1441-1447, 45, American Association for Aerosol Research.

Lin et al., "Aerosol Processing of Low-Cost Mesoporous Silica Spherical Particles from Photonic Industrial Waste Powder for C02 Capture", Chemical Engineering Journal, 2012, 215-222, 197, Elsevier B.V.

Liu et al., "Alumina with Various pore Structures Prepared by Spray Pyrolysis of Inorganic Aluminum Precursors", I&EC Research, 2013, 52, 13377-13383, ACS Publications.

Lu et al., "Aersol-Assisted Self-Assembly of Mesostructured Spherical Nanoparticles", Nature, 1999, vol. 398, Macmillan Magazines Ltd.

Maksasithorn, Surasa et al., "Preparation of super-microporous WO3—SiO2 olefin metathesis catalysts by the aerosol-assisted sol-gel process", pp. 125-133, Microporous and Mesoporous Materials 213 (2015).

Notice of Allowance pertaining to U.S. Appl. No. 15/146,037, filed May 4, 2016, 8 pages.

Non-Final Office Action dated Sep. 25, 2017 pertaining to U.S. Appl. No. 15/252,733, filed Aug. 31, 2016.

Xie et al., "An Overview of Recent Development in Composite Catalysts from Porous Materials for Various Reactions and Processes", Int. J. Mol. Sci. 11, pp. 2152-2187, 2010.

Notice of Allowance pertaining to U.S. Appl. No. 15/252,733, filed Aug. 31, 2016, 8 pages.

(56) References Cited

OTHER PUBLICATIONS

Popoff et al., "Expanding the scope of metathesis: a survey of polyfunctional, single-site supported tungsten systems for hydrocarbon valorization", Chemical Society Reviews, Issue 23 (2013).
Mazoyer, et al., "Production of propylene from 1-butene on highly active "Bi-functional single active site" catalyst: Tungsten carbene-hydride supported on alumina", http://dialog.proqquest.com/professional/printviewfile?accountid=157282—Accessed: Jul. 6, 2017.
Office Action pertaining to U.S. Appl. No. 15/949,726, dated Jun. 7, 2018.
International Search Report and Written Opinion dated Dec. 3, 2018 pertaining to International Application No. PCT/US2018/046696 filed Aug. 14, 2018.
International Search Report and Written Opinion dated May 24, 2019 pertaining to International application No. PCT/US2019/018541 filed Feb. 19, 2019, 17 pgs.
Senthilkumar et al. "Studies on growth and characterization of heterogeneous tungsten oxide nanostructures for photoelectrochemical and gas sensing applications", Applied Surface Science, vol. 362, pp. 102-108, 2016.
Office Action dated Jan. 24, 2020 pertaining to U.S. Appl. No. 16/256,641, filed Jan. 24, 2019, 7 pgs.
International Search Report and Written Opinion dated Apr. 9, 2020 pertaining to International application No. PCT/US2020/012309 filed Jan. 6, 2020, 12 pgs.

\* cited by examiner

AEROSOL PROCESSING METHOD FOR CONTROLLED COATING OF SURFACE SPECIES TO GENERATE CATALYSTS

CROSS-REFERENCE TO RELATED APPLICATIONS

This application claims priority to U.S. Provisional Patent Application Ser. No. 62/546,765 filed Aug. 17, 2017 entitled AEROSOL PROCESSING METHOD FOR CONTROLLED COATING OF SURFACE SPECIES TO GENERATE CATALYSTS, which is incorporated by reference in the present disclosure in its entirety.

TECHNICAL FIELD

Embodiments of the present disclosure generally relate to synthesis of catalytic materials.

BACKGROUND

In recent years, there has been a dramatic increase in the demand for propene to feed the growing markets for polypropylene, propylene oxide, and acrylic acid. Currently, most of the propene produced worldwide (74 million tons/year) is a by-product from steam cracking units (57%), which primarily produce ethylene, or a by-product from Fluid Catalytic Cracking (FCC) units (30%), which primarily produce gasoline. These processes cannot respond adequately to a rapid increase in propene demand.

Raffinate is the residue C4 stream from a naphtha cracking process or from a gas cracking process when components are removed (the C4 stream typically containing, as its chief components, n-butane, 1-butene, 2-butene, isobutene and 1,3-butadiene, and optionally some isobutane and said chief components together forming up to 99% or more of the C4 stream). Specifically, Raffinate-2 is the C4 residual obtained after separation of 1,3-butadiene and isobutene from the C4 raffinate stream and consists mainly of cis- or trans-2-butene, 1-butene, and n-butane. Similarly, Raffinate-3 is the C4 residual obtained after separation of 1,3-butadiene, isobutene, and 1-butene from the C4 raffinate stream and consists mainly of cis- or trans-2-butene, n-butane, and unseparated 1-butene. Utilizing Raffinate-2 and Raffinate-3 streams for conversion to propene is desirable to increase the available supply of propene.

Development of metathesis catalysts to convert Raffinate-2 and Raffinate-3 streams to propene have relied on wet impregnation to impregnate a metal oxide into a previously synthesized support material or on including a metal oxide into a premixture that is formed into the catalyst support material. However, wet impregnation or including the metal oxide into the catalyst premix are limited in that a large proportion of the metal oxide is bound in the interior portions of the catalyst support material and likely less accessible to reactants of the metathesis reaction. Additionally, control of the properties of the resulting metathesis catalyst is limited.

SUMMARY

Accordingly, ongoing needs exist for improved methods of synthesizing catalysts. Embodiments of the present disclosure are directed to methods of synthesizing catalysts via aerosol processing to deposit a catalytically active compound on surfaces of catalyst support particles, where the surfaces are accessible to gases and vapors.

According to some embodiments, a method of producing a catalyst may include generating an aerosolized flow of catalyst support particles, evaporating a catalytically active compound precursor to produce a catalytically active compound precursor vapor, contacting the aerosolized flow of catalyst support particles with the catalytically active compound precursor vapor, and condensing the catalytically active compound precursor to produce the catalyst that may include a catalytically active compound deposited on surfaces of the catalyst support particles.

According to other embodiments, a method of producing a catalyst may include aerosolizing a catalyst support precursor mixture comprising a catalyst support precursor and a diluent to produce an aerosolized catalyst support precursor mixture, passing the aerosolized catalyst support precursor mixture to a first heating zone, and drying the aerosolized catalyst support precursor mixture in the first heating zone to form a plurality of aerosolized catalyst support particles. The method may further include passing the plurality of aerosolized catalyst support particles to a second heating zone downstream of the first heating zone, contacting the plurality of aerosolized catalyst support particles with a catalytically active compound precursor vapor in the second heating zone, and condensing the catalytically active compound precursor vapor to produce the catalyst comprising a catalytically active compound deposited on surfaces of the catalyst support particles.

According to yet other embodiments, a catalyst is disclosed that may be prepared by a process that may include the steps of generating an aerosolized flow of catalyst support particles, evaporating a catalytically active compound precursor to produce a catalytically active compound precursor vapor, contacting the aerosolized flow of catalyst support particles with the catalytically active compound precursor vapor, and condensing the catalytically active compound precursor to produce the catalyst comprising a catalytically active compound deposited on surfaces of the catalyst support particles.

According to still other embodiments, a catalyst may include a plurality of catalyst support particles comprising silica, alumina, or silica and alumina and a catalytically active compound deposited onto surfaces of a plurality of catalyst support particles. The surfaces of the plurality of catalyst support particles may be accessible to gases and vapors, and the catalytically active compound may include tungsten. The catalytically active compound may be deposited on from 1% to 50% of the surfaces of the catalyst support particles that are accessible to gases and vapors.

In still other embodiments, a system for producing a catalyst may include an aerosolizing unit, a first heating zone downstream of the aerosolizing unit, and a second heating zone downstream of the first heating zone. The second heating zone may comprise an inlet configured to introduce a catalytically active compound precursor to the second mixing zone. An aerosolized catalyst support precursor mixture may be configured to be aerosolized by the aerosolizing unit and may flow through the first heating zone and then the second heating zone.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
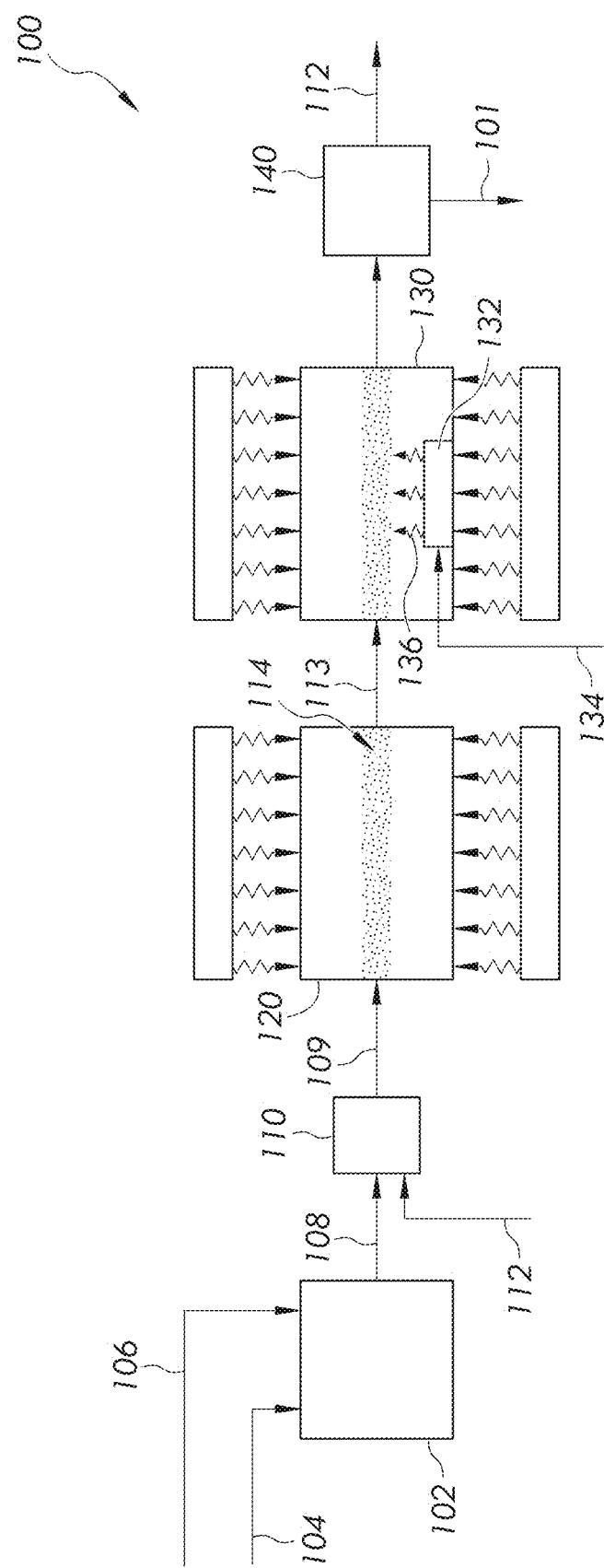
FIG. 1 schematically depicts an aerosol processing system, in accordance with one or more embodiments of the present disclosure.

For the purpose of describing the simplified schematic illustrations and descriptions of FIGS. 1-5, the numerous valves, temperature sensors, electronic controllers, and the like that may be employed and well known to those of ordinary skill in the art of certain chemical processing operations are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1-5. Mixing or combining may also include mixing by directly introducing both streams into a like system component, such as a vessel, aerosolizer, heating zone, furnace, or other system component. For example, it should be understood that when two streams are depicted as being combined directly prior to entering a system component, the streams could equivalently be introduced into the system component and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to catalysts and methods of synthesizing catalysts via aerosol processing to deposit a catalytically active compound on surfaces of catalyst support particles accessible to gases and vapors. In embodiments, a method of forming a catalyst comprises generating an aerosolized flow of catalyst support particles, vaporizing a catalytically active compound precursor to produce a catalytically active compound precursor vapor, contacting the aerosolized flow of catalyst support particles with the catalytically active compound precursor vapor, and condensing the catalytically active compound precursor vapor to produce the catalyst comprising the catalytically active compound deposited on surfaces of the catalyst support particles.

The methods of producing catalysts described in this disclosure allow for continuous synthesis of catalysts having a catalytically active compound deposited on a surface of the catalyst support particles. By depositing the catalytically active compound on the surfaces of the catalyst support particle that are accessible to gases and vapors, the catalytically active compound is accessible to reactants rather than being buried or partially buried in the interior of the catalyst support material and inaccessible to the reactants. The catalytically active compound deposited on the surface of the catalyst support particles by the aerosol processing methods described in this disclosure are highly active. The catalysts formed by the disclosed methods provide performance equivalent to state-of-the-art catalysts having higher loading of the catalytically active compound. In some examples, the catalysts synthesized by the aerosol processing methods described in this disclosure have an amount of catalytically active compound less than 50%, or even less than 25% of the catalytically active compound of conventionally prepared catalysts. The catalysts synthesized by the aerosol processing methods of this disclosure provide catalytic activity that is equivalent to or superior to the catalytic activity performance of conventionally prepared catalysts.

As used in this disclosure, a "catalyst" refers to a solid particulate comprising catalyst support particles and at least one catalytically active compound.

As used in this disclosure, a "catalytically active compound" refers to any substance which increases the rate of a specific chemical reaction. Catalysts described in this disclosure may be utilized to promote various reactions, such as, but not limited to, isomerization, metathesis, cracking, hydrogenation, demetallization, desulfurization, denitrogenation, other reactions, or combinations of these.

As used in this disclosure, "catalytic activity" refers to a degree to which the catalyst increases the reaction rate of a reaction. Greater catalytic activity of a catalyst increases the reaction rate of a reaction compared to a catalyst having a lesser catalytic activity.

The catalysts synthesized by the aerosol processing systems and methods generally comprise catalyst support particles having a catalytically active compound deposited on the surfaces of the catalyst support particles. The catalyst support particles may include silica, alumina, or a combination of silica and alumina.

The catalytically active compound may be a metal, metal oxide, other catalytically active compound, or combinations of these. In some embodiments, the catalytically active compound may be a metal, such as platinum, gold, palladium, rhodium, iridium, chromium, other metal, or combinations of these. Alternatively, the catalytically active compound may include a metal oxide, such as one or more than one oxide of a metal from Groups 6-10 of the IUPAC Periodic Table. In some embodiments, the metal oxide may include at least one oxide of molybdenum, rhenium, tungsten, manganese, titanium, cerium or any combination of these. In some embodiments, the metal oxide may be tungsten oxide. The morphology, type, and amount of the catalytically active compound deposited on the surface of the catalyst support may determine the catalytic activity of the catalyst. The following methods and systems are described in the context of synthesizing isomerization catalysts, metathesis catalysts, or isomerization and metathesis catalysts having a metal oxide as the catalytically active compound deposited on the surface of a catalyst support particle. However, it is understood that the methods and system may be utilized to synthesize other types of catalysts.

A method of synthesizing the catalyst having the catalytically active compound deposited on the surface of the catalyst support in accordance with at least one embodiment of this disclosure includes generating an aerosolized flow of catalyst support particles, vaporizing or evaporating a catalytically active compound precursor to produce a catalytically active compound precursor vapor, contacting the aerosolized flow of catalyst support particles with the catalytically active compound precursor vapor, and condensing the catalytically active compound precursor vapor to produce the catalyst comprising the catalytically active compound deposited on the surface of the catalyst support particles. In some embodiments, the catalytically active compound precursor vapor may condense directly onto the surface of the catalyst support particles. Directly depositing the catalytically active compound precursor vapor onto the surface of the catalyst support particles may include heterogeneous nucleation of the catalytically active compound precursor vapor on the surfaces of the catalyst support particles. Additionally, in some embodiments, the catalytically active compound may condense onto catalytically active compound previously deposited on the catalyst support particle, which may grow the additionally deposited catalytically active compound into small clusters/particles on the surface of the catalyst support particles if the vapor preferentially deposits onto (or migrates to) the previously deposited catalytically active material. Alternatively, in some embodiments, the catalytically active compound precursor vapor may condense onto itself (homogeneous nucleation) to create clusters or particles of the catalytically active compound, which may then then diffuse to the catalyst support particles and deposit onto the surface of the catalyst support particles. The aerosolized flow of catalyst support particles may be generated by aerosolizing a catalyst support precursor mixture and drying, reacting, or drying and reacting the aerosolized catalyst support precursor mixture to form the catalyst support particles. The aerosol processing method may be a continuous process to continuously produce the catalyst from the catalyst support precursor and the catalytically active compound precursor.

Referring to FIG. 1, an aerosol processing system 100 for synthesizing the catalyst 101 comprising a catalytically active compound deposited on the surfaces of a catalyst support is depicted. As shown in FIG. 1, the aerosol processing system 100 includes a vessel 102 for mixing at least a catalyst support precursor 104 and a diluent 106 to form a catalyst support precursor mixture 108. The aerosol processing system 100 further includes an aerosolizing unit 110, a first heating zone 120 downstream of the aerosolizing unit 110, and a second heating zone 130 downstream of the first heating zone 120. The catalyst support precursor mixture 108 is passed to the aerosolizing unit 110. The aerosolizing unit 110 aerosolizes the catalyst support precursor mixture 108 into a plurality of droplets of the catalyst support precursor mixture, referred to in this disclosure as the aerosolized catalyst support precursor mixture 109. A carrier gas 112 introduced to the aerosolizing unit 110 conveys the aerosolized catalyst support precursor mixture 109 out of the aerosolizing unit 110 and through the first heating zone 120, in which the droplets of the aerosolized catalyst support precursor mixture 109 are dried, reacted, or both to form a plurality of solid catalyst support particles 114 aerosolized in an aerosol 113 comprising the carrier gas 112 and the catalyst support particles 114.

The aerosol 113 comprising the carrier gas 112 and the catalyst support particles 114 passes into and through the second heating zone 130. The second heating zone 130 may include a source 132 of a catalytically active compound precursor 134. Heat from the second heating zone 130 causes the catalytically active compound precursor 134 in the source 132 to vaporize to form a catalytically active compound precursor vapor 136. The catalytically active compound precursor vapor 136 may contact the plurality of catalyst support particles 114 in the aerosol 113 and may condense on the surfaces of the catalyst support particles 114 to form the catalyst 101. Once condensed onto the catalyst support particles 114, the catalytically active compound may undergo surface diffusion, in which the atoms, molecules, or both of the catalytically active compound may migrate on the surface of the catalyst support particles 114 until the atoms, molecules, or both reach a favorable energy state. In some embodiments, the catalytically active compound precursor vapor 136 may homogeneously nucleate to form catalytically active compound clusters or particles that may then contact the plurality of catalyst support particles 114 and deposit on the surfaces of the catalyst support particles 114 to form the catalyst 101. In some embodiments, the catalytically active compound clusters or particles may have a particle size of up to 20 nanometers (nm). In some embodiments, the aerosol processing system 100 may include a separator 140 for separating the catalyst 101 from the carrier gas 112 and collecting the catalyst 101.

The catalyst support precursor 104 may include a silica precursor, an alumina precursor, or combinations of these. Examples of the silica precursor in the catalyst support precursor 104 may include, but are not limited to, fumed silica, colloidal silica, silane ($SiH_4$), silicon tetrachloride, tetraethyl orthosilicate (TEOS), or combinations of these. In some embodiments, the silica precursor may include fumed silica. In embodiments, the catalyst support precursor 104 may include a plurality of precursor materials, such as a combination of silica precursors and alumina precursors for example. In some embodiments, the catalyst support precursor 104 may comprise from 0.1 weight percent (wt. %) to 99.9 wt. % silica precursor, based on the total weight of the catalyst support precursor 104 prior to combining the catalyst support precursor 104 with the diluent 106 to make the catalyst support precursor mixture 108. In embodiments, the catalyst support precursor 104 may include from 0.1 wt. % to 95 wt. %, from 0.1 to 90 wt. %, from 0.1 wt. % to 75 wt. %, from 0.1 wt. % to 50 wt. %, from 0.1 wt. % to 25 wt. %, from 0.1 wt. % to 10 wt. %, from 10 wt. % to 99.9 wt. %, from 10 wt. % to 95 wt. %, from 10 wt. % to 90 wt. %, from 10 wt. % to 75 wt. %, from 10 wt. % to 50 wt. %, from 10 wt. % to 25 wt. %, from 25 wt. % to 99.9 wt. %, from 25 wt. % to 95 wt. %, from 25 wt. % to 90 wt. %, from 25 wt. % to 75 wt. %, from 25 wt. % to 50 wt. %, from 50 wt. % to 99.9 wt. %, from 50 wt. % to 95 wt. %, from 50 wt. % to 90 wt. %, from 50 wt. % to 75 wt. %, from 75 wt. % to 99.9 wt. %, from 75 wt. % to 95 wt. %, from 75 wt. % to 90 wt. %, or from 90 wt. % to 99.9 wt. % silica precursor, based on the total weight of the catalyst support precursor 104 prior to combining the catalyst support precursor 104 with the diluent 106 to make the catalyst support precursor mixture 108.

Examples of alumina precursors may include, but are not limited to, aluminum nitrate ($Al(NO_3)_3$), fumed alumina, aluminum salts such as $AlCl_3$, $AlPO_4$, or $Al_2(SO_4)_3$ and their hydrates, other alumina precursors, or combinations of these. In some embodiments, the alumina precursor may comprise aluminum nitrate ($Al(NO_3)_3$). In some embodiments, the catalyst support precursor 104 may include from 0.0 wt. % to 99.8 wt. % alumina precursor, based on the total weight of the catalyst support precursor 104 prior to combining the catalyst support precursor 104 with the diluent 106 to make the catalyst support precursor mixture 108. In other examples, the catalyst support precursor 104 may include from 0.0 wt. % to 95 wt. %, from 0.0 to 90 wt. %, from 0.0 wt. % to 75 wt. %, from 0.0 wt. % to 50 wt. %, from 0.0 wt. % to 25 wt. %, from 0.0 wt. % to 10 wt. %, from 0.1 wt. % to 99.8 wt. %, from 0.1 wt. % to 95 wt. %, from 0.1 wt. % to 90 wt. %, from 0.1 wt. % to 75 wt. %, from 0.1 wt. % to 50 wt. %, from 0.1 wt. % to 25 wt. %, from 10 wt. % to 99.8 wt. %, from 10 wt. % to 95 wt. %, from 10 wt. % to 90 wt. %, from 10 wt. % to 75 wt. %, from 10 wt. % to 50 wt. %, from 25 wt. % to 99.8 wt. %, from 25 wt. % to 95 wt. %, from 25 wt. % to 90 wt. %, from 50 wt. % to 99.8 wt. %, from 50 wt. % to 95 wt. %, from 50 wt. % to 90 wt. %, from 75 wt. % to 99.8 wt. %, or from 75 wt. % to 95 wt. % alumina precursor, based on the total weight of the catalyst support precursor 104 prior to combining the catalyst support precursor 104 with the diluent 106 to make the catalyst support precursor mixture 108.

In some embodiments, the catalyst support precursor mixture 108 may optionally include one or a plurality of dopants. The catalyst support precursor mixture 108 may include a dopant to modify one or more than one characteristic or property of the catalyst support particles 114 formed from the catalyst support precursor mixture 108. Examples of dopants may include, but are not limited to, titania, rhenia, phosphates, or combinations of these. Additionally, dopants may include inert constituents, sacrificial constituents, or both, in the catalyst support precursor mixture 108. Non-limiting examples of inert and sacrificial constituents may include polystyrene latex, other polymers, or combinations of polymers. When heated to high temperatures, the polystyrene latex burns off, leaving pores where the polystyrene latex was previously. These inert and sacrificial constituents may be used to modify the surface area of the catalyst support particles 114. Synthesis of the catalyst 101 via aerosol processing allows for the inclusion of dopants during initial synthesis of the catalyst support particles 114 as compared to applying one or a plurality of dopant compounds to the catalyst 101 using a post-synthesis addition process, such as a coating process for example. In embodiments, one or more than one dopant may be included in the catalyst support precursor mixture 108 such that the dopant(s) are thus included in and distributed throughout the catalyst support particles 114 during the aerosol processing.

The diluent 106 may be water, an organic solvent, or a combination of water and at least one organic solvent. Example organic solvents may include methanol, ethanol, acetone, or a combination of solvents. In some embodiments, the diluent 106 may be water such that the catalyst support precursor mixture 108 is an aqueous catalyst support precursor mixture. In other embodiments, the diluent 106 may include a combination of water and at least one organic solvent. In some embodiments, the catalyst support precursor mixture 108 may be absent a surfactant. Inclusion of a surfactant in the catalyst support precursor mixture 108 may require an additional calcination step to prepare the catalyst 101. In some cases, the presence of a surfactant in the catalyst support precursor mixture 108 may result in an undesired residue on the catalyst 101 which may degrade the performance of the catalyst 101 and/or be toxic or hazardous to health. The catalyst support precursor mixture 108 may be formed as a solution, a suspension, or both of the catalyst support precursor 104 in the diluent 106. For example, with fumed catalyst support precursors, such as fumed silica precursors or fumed alumina precursors, or colloidal precursors, a suspension is formed for the catalyst support precursor mixture 108. Alternatively, for a catalyst support precursor 104 comprising metal salts, the catalyst support precursor mixture 108 may be a solution of the catalyst support precursor 104 in the diluent 106. In some embodiments, the catalyst support precursor 104 may include fumed silica precursor or fumed alumina precursor and a metal salt such that the catalyst support precursor mixture 108 comprises a suspension of the fumed components in a solution comprising the metal salt dissolved in the diluent 106.

The catalyst support precursor mixture 108 may have an amount of the catalyst support precursor 104 sufficient so that the diluent is removed to form the solid catalyst support particles 114 from the droplets of the catalyst support precursor mixture 108 during the residence time in the first heating zone 120. In embodiments, the catalyst support precursor mixture 108 may have from 1 wt. % to 20 wt. % catalyst support precursor 104, based on the total weight of the catalyst support precursor mixture 108. In other embodiments, the catalyst support precursor mixture 108 may comprise from 1 wt. % to 16 wt. %, from 1 wt. % to 12 wt. %, from 1 wt. % to 8 wt. % from 1 wt. % to 4 wt. %, from 4 wt. % to 20 wt. %, from 4 wt. % to 16 wt. %, from 4 wt.

% to 12 wt. %, from 4 wt. % to 8 wt. %, from 8 wt. % to 20 wt. %, from 8 wt. % to 16 wt. %, from 8 wt. % to 12 wt. %, from 12 wt. % to 20 wt. %, from 12 wt. % to 16 wt. %, or from 16 wt. % to 20 wt. % catalyst support precursor 104, based on the total weight of the catalyst support precursor mixture 108. In some embodiments, one or a plurality of dopants may be mixed with the catalyst support precursor mixture 108 prior to aerosolizing the catalyst support precursor mixture 108.

The catalyst support precursor mixture 108 may be aerosolized to form an aerosolized catalyst support precursor mixture 109, which comprises a plurality of droplets of the catalyst support precursor mixture 108 dispersed in the carrier gas 112. As shown in FIG. 1, the catalyst support precursor mixture 108 may be aerosolized in the aerosolizing unit 110 to form the aerosolized catalyst support precursor mixture 109. A variety of aerosolizing units 110 are envisioned, as long as they generate a liquid spray of droplets. Examples of aerosolizing units 110 may include, but are not limited to, ultrasonic transducers, spray nozzles, other aerosolizing devices, or combinations of these. In some embodiments, an ultrasonic transducer may be used to generate the aerosolized catalyst support precursor mixture 109. Ultrasonic transducers may be readily scalable and highly controllable.

The type of aerosolizing unit 110 and the specifications of the aerosolizing unit 110 may influence the particle size of the catalyst support particles 114 by influencing the average droplet size of the aerosolized catalyst support precursor mixture 109. For example, an aerosolizing unit 110 configured to produce smaller sized droplets will generally result in smaller catalyst support particles 114 produced by the aerosol processing method. The type, specifications, or both of the aerosolizing unit 110 may also influence the particle size of the catalyst support particles 114 by increasing the turbulence of the aerosolized catalyst support precursor mixture 109, which may cause some droplets to collide and combine into larger droplets. In some embodiments, the aerosolizing unit 110 may be capable of producing droplets of the catalyst support precursor mixture 108 having droplet sizes from 0.1 µm to 100 µm, from 0.1 µm to 20 µm, from 0.5 µm to 100 µm, or from 0.5 µm to 20 µm.

As previously discussed, a carrier gas 112 is introduced to the aerosolizing unit 110. The aerosolized catalyst support precursor mixture 109 is aerosolized in the carrier gas 112, which then transports the droplets of the aerosolized catalyst support precursor mixture 109 through the heating zones, such as the first heating zone 120 and the second heating zone 130. In some embodiments, the carrier gas 112 is air. Alternatively, in other embodiments, the carrier gas 112 may include at least one of nitrogen, argon, helium, or combinations of these gases. In yet further embodiments, the carrier gas 112 may include a mixture that contains a reactant or dopant for the formation of the catalyst support particles 114. For example, the carrier gas 112 may include silane ($SiH_4$). The selection of a non-reactive gas or a reactive gas or a combination of both for the carrier gas 112 depends on the catalyst support precursors 104 utilized and the desired properties of the catalyst 101.

In some embodiments, the method of synthesizing the catalyst may include aerosolizing a dopant stream concurrently with aerosolizing the catalyst support precursor mixture 108 to form an aerosol comprising the aerosolized catalyst support precursor mixture 109 and the aerosolized dopant.

Referring to FIG. 1, the aerosolized catalyst support precursor mixture 109 is passed to and through at least a first heating zone 120 and a second heating zone 130 downstream of the first heating zone 120 to form the catalyst 101. The method of synthesizing the catalyst 101 includes drying the aerosolized catalyst support precursor mixture 109, reacting the aerosolized catalyst support precursor mixture 109, or both in the first heating zone 120 to form a plurality of catalyst support particles 114. The droplets of aerosolized catalyst support precursor mixture 109 are passed to the first heating zone 120, in which heat from the first heating zone 120 dries the droplets of the aerosolized catalyst support precursor mixture 109 to form the plurality of catalyst support particle 114. In some embodiments, the first heating zone 120 may be a region of a first furnace, and the carrier gas 112 may convey the droplets of the aerosolized catalyst support precursor mixture 109 through the region of the first furnace. Alternatively, the first heating zone 120 may comprise a first section of a reaction tube disposed within the first furnace, and the carrier gas 112 may convey the droplets of the aerosolized catalyst support precursor mixture 109 through the reaction tube. In these embodiments having the reaction tube, the heat from the furnace may be transferred to the reaction tube, conducted through the wall of the reaction tube, and then transferred to the droplets of the aerosolized catalyst support precursor mixture 109 flowing through the reaction tube.

In addition to drying the droplets of the aerosolized catalyst support precursor mixture 109, the first heating zone 120 may initiate formation of crystallinity within the catalyst support particles 114 formed from drying the droplets of aerosolized catalyst support precursor mixture 109. It is noted that the aerosolized catalyst support precursor mixture 109 need not be fully dried prior to initiation of crystallization. As the aerosolized catalyst support precursor mixture 109 passes through the first heating zone 120, the droplets of the aerosolized catalyst support precursor mixture 109 begin to dry and the catalyst support precursor 104 becomes more concentrated in each of the droplets. Subsequently, as the droplets are heated further, the dried or partially dried catalyst support precursor 104 can react to form amorphous structures, crystalline structures, or a combination of amorphous and crystalline structures depending upon the catalyst support precursor chemistry.

In alternative embodiments, one or more reactive gases may be introduced to the first heating zone 120 and may decompose at high temperatures in the first heating zone 120, react in the first heating zone 120, and nucleate to form the plurality of catalyst support particles 114. For example, a reactive gas, such as but not limited to $SiH_4$, may be introduced to the first heating zone 120. The $SiH_4$ may thermally decompose in the first heating zone 120 to produce silicon atoms (Si) and hydrogen molecules ($H_2$). In the presence of oxygen ($O_2$) in the first heating zone 120, the silicon (Si) may react with the oxygen gas ($O_2$) to produce $SiO_2$. This $SiO_2$ may nucleate in the first heating zone 120 to produce $SiO_2$ particles. The $SiO_2$ particles may grow in size through continued decomposition of $SiH_2$, reaction of Si with $O_2$ to produce $SiO_2$, and condensation of $SiO_2$ onto the $SiO_2$ particles to produce the plurality of catalyst support particles 114.

In still other embodiments, the reactive gas may be introduced to the first heating zone 120 and may decompose in the first heating zone 120 to deposit a secondary material onto the surfaces of the catalyst support particles 114. For example, $SiH_4$ may be introduced to the first heating zone 120, may decompose into Si and $H_2$, and react with $O_2$ to form $SiO_2$. In these examples, the $SiO_2$ may condense on the outer surfaces of the catalyst support particles 114 formed from the aerosolized catalyst support precursor mixture 109. In some embodiments, the SiO$_2$ formed from decomposition of SiH$_4$ may condense onto the droplets of aerosolized catalyst support precursor mixture 109 in the first heating zone 120 to include the SiO$_2$ into the catalyst support particles 114. Although described in the context of SiH$_4$, other reactive gases are contemplated.

In embodiments, the first heating zone 120 may be maintained at a temperature sufficient to evaporate, react, or decompose the diluent 106 from the droplets of the aerosolized catalyst support precursor mixture 109 to form a plurality of solid catalyst support particles 114. In embodiments, the first heating zone 120 may be maintained at a first temperature of from 200° C. to 1500° C. In other embodiments, the first heating zone may be maintained at a temperature of from 200° C. to 1450° C., from 200° C. to 1400° C., from 200° C. to 1300° C., from 500° C. to 1500° C., 500° C. to 1450° C., from 500° C. to 1400° C., from 500° C. to 1300° C., from 600° C. to 1500° C., 600° C. to 1450° C., from 600° C. to 1400° C., from 600° C. to 1300° C., from 1000° C. to 1500° C., 1000° C. to 1450° C., from 1000° C. to 1400° C., from 1000° C. to 1300° C., from 1300° C. to 1500° C., 1300° C. to 1450° C., from 1300° C. to 1400° C., or from 1400° C. to 1500° C. In further embodiments, to merely dry the droplets of the aerosolized catalyst support precursor mixture 109, the first heating zone 120 may be heated to a temperature from 200° C. to 800° C. If the temperature in the first heating zone 120 is too great, the droplets of the aerosolized catalyst support precursor mixture 109 may rapidly dry to form a shell structure of the catalyst support precursor 104 rather than solid catalyst support particles 114. Catalyst support shells are less able to withstand the stress and pressures exerted on the catalyst 101 during downstream processing, use, or both compared to the solid catalyst support particles 114.

In some embodiments, the first heating zone 120 may comprise a plurality of temperature zones. Each of the temperature zones may operate at a different temperature. For example, a first temperature zone operated at a temperature of from 200° C. to 800° C. may be utilized to at least partially dry or fully dry the droplets of the aerosolized catalyst support precursor mixture 109, and a second temperature zone operated at a temperature of from 800° C. to 1500° C. may be utilized to react the catalyst support precursors 104, crystallize the catalyst support precursors 104, or both to form the catalyst support particles 114. In embodiments, the first heating zone 120 may be operated at ambient pressure.

The residence time of the aerosolized catalyst support precursor mixture 109 in the first heating zone 120 may be sufficient to produce fully dried and reacted catalyst support particles 114. In some embodiments, the residence time of the aerosolized catalyst support precursor mixture 109 in the first heating zone 120 may be from 0.1 seconds to 9 seconds. In other embodiments, the residence time of the aerosolized catalyst support precursor mixture 109 in the first heating zone 120 may be from 0.1 seconds to 8 seconds, 0.1 second to 6 seconds, from 0.1 second to 4 seconds, from 0.5 second to 9 seconds, from 0.5 seconds to 8 seconds, from 0.5 seconds to 6 seconds, from 0.5 second to 4 seconds, from 1 second to 9 seconds, from 1 second to 8 seconds, from 1 second to 6 seconds, from 1 second to 4 seconds, from 2 seconds to 9 seconds, from 2 seconds to 8 seconds, from 2 seconds to 6 seconds, or from 2 seconds to 4 seconds. If the residence time is of insufficient duration, the droplets of the aerosolized catalyst support precursor mixture 109 may not dry sufficiently and may be left unreacted such that the catalyst support particles 114 are not formed. Conversely, if the residence time is too great, energy is wasted and the catalyst support particles 114 may be lost to the furnace walls or grow too large in size due to collisions with other catalyst support particles 114. Additionally, drying the droplets of the aerosolized catalyst support precursor mixture 109 too rapidly, such as by decreasing the residence time too much, increasing the temperature in the first heating zone 120 too much, or both, can lead to catalyst support shells, which can collapse under further processing, instead of solid catalyst particles 114, as previously described.

The feed rate of the aerosolized catalyst support precursor mixture 109 into and through the first heating zone 120 may be determined by the flowrate of the carrier gas 112. In general, the faster the flowrate of the carrier gas 112, the higher the feed rate of the aerosolized catalyst support precursor mixture 109 into the first heating zone 120. The carrier gas 112 flowrate may also influence the residence time of the aerosolized catalyst support precursor mixture 109 in the first heating zone 120. Increasing the carrier gas 112 flowrate may reduce the residence time. Conversely, decreasing the carrier gas 112 flowrate may increase the residence time. In embodiments, the carrier gas 112 flowrate may be sufficient to maintain an aerosolized and fluidized flow of droplets of the aerosolized catalyst support precursor mixture 109 through the first heating zone 120 but not so much that the residence time of the aerosolized catalyst support precursor mixture 109 is not sufficient to fully form the catalyst support particles 114. In some embodiments, the carrier gas 112 flowrate may be sufficient to achieve a residence time of the aerosolized catalyst support particles 114 in the first heating zone 120 and the second heating zone 130 of from 0.1 seconds to 10 seconds, from 0.1 seconds to 9 seconds, from 0.1 seconds to 8 seconds, 0.1 second to 6 seconds, from 0.1 second to 4 seconds, from 0.5 seconds to 10 second, from 0.5 seconds to 9 seconds, from 0.5 seconds to 8 seconds, from 0.5 seconds to 6 seconds, from 0.5 seconds to 4 seconds, from 1 second to 10 seconds, from 1 second to 9 seconds, from 1 second to 8 seconds, from 1 second to 6 seconds, from 1 second to 4 seconds, from 2 seconds to 10 seconds, from 2 seconds to 9 seconds, from 2 seconds to 8 seconds, from 2 seconds to 6 seconds, or from 2 seconds to 4 seconds. For embodiments in which the aerosolizing unit comprises one or a plurality of ultrasonic transducers, the carrier gas 112 flowrate may be from 1.25 liters per min (L/min) to 3.75 L/min per transducer. Alternatively, the carrier gas 112 flowrate may be greater than 3.75 L/min or less than 1.25 L/min depending on the size of the equipment (i.e., first heating zone 120, second heating zone 130, aerosolizing unit 110, etc.) of the aerosol processing system 100.

Referring again to FIG. 1, once the catalyst support particles 114 are formed, the aerosol 113 may comprise the carrier gas 112 and the catalyst support particles 114. The aerosol 113 may then be passed to a second heating zone 130 where a catalytically active compound may be deposited onto the surface of the plurality of catalyst support particles 114. The second heating zone 130 may be in tandem with the first heating zone 120, meaning that the second heating zone 130 is positioned downstream of the first heating zone 120. The catalyst support particles 114 may be passed to and through the second heating zone 130 by the carrier gas 112. In some embodiments, the second heating zone 130 may be a second furnace, more specifically, a region in a second furnace. Alternatively, the second heating zone 130 may comprise another region of the first furnace separate from the first heating zone 120. In some embodiments, the second heating zone 120 may be a second section of a reaction tube that extends through a second furnace or another region of the first furnace. In the second heating zone 130, the catalyst support particles 114 may be contacted with the catalytically active compound precursor vapor 136. Although the aerosol processing systems 100 and methods are described in this disclosure as having at least a first heating zone 120 and a second heating zone 130, it is contemplated that the aerosol processing systems 100 may have more than two heating zones. Additionally, it is contemplated that the first heating zone 120, the second heating zone 130, or both may include multiple temperature regions, which may be independently controlled at different temperatures.

As illustrated in FIG. 1, in some embodiments, the second heating zone 130 may include a source 132 of the catalytically active compound precursor vapor 136. In the embodiment shown in FIG. 1, the source 132 of the catalytically active compound precursor vapor 136 may include a crucible or other open vessel containing a catalytically active compound precursor. Heat from the second heating zone 130 may be transferred to the source 132 and the catalytically active compound precursor contained within the source 132. The heat from the second heating zone 130 may cause the catalytically active compound precursor to vaporize to form the catalytically active compound precursor vapor 136. Alternatively, in some embodiments, the source 132 of the catalytically active compound precursor vapor 136 may be heated independently of the second heating zone 130. For example, the source 132 may include a supplemental heat source that may be controlled independent of the second heating zone 130. The catalytically active compound precursor may transfer/vaporize into the vapor phase through evaporation, sublimation, reaction/decomposition, melting, or combinations of these, for example. The catalytically active compound precursor vapor 136 may distribute throughout the second heating zone 130. In embodiments, a catalytically active compound precursor stream 134 comprising the catalytically active compound precursor may be continuously introduced to the source 132 to maintain continuous generation of the catalytically active compound precursor vapor 136 in the second heating zone 130.

The catalytically active compound precursor 134 may comprise a metal, metal salt, metallate such as a metal oxide for example, other catalytically active compound precursors, or combinations of these. The catalytically active compound precursor 134 may be any metal or metal oxide that can be vaporized to produce the catalytically active compound precursor vapor 136. Alternatively, the catalytically active compound precursor 134 may be a metal salt that can be solubilized in a diluent and atomized or aerosolized. In some embodiments, the catalytically active compound precursor 134 may include a metal such as platinum, gold, palladium, rhodium, iridium, chromium, other metal, or combinations of these. Alternatively, the catalytically active compound precursor 134 may include a metallate precursor, such as an oxymetallate precursor for example. The metal of the metallate precursor may include one or more than one metals from Groups 6-10 of the IUPAC Periodic Table. In some embodiments, the metal of the metallate precursor may include at least one of molybdenum, rhenium, tungsten, manganese, titanium, cerium, or any combination of these. In some embodiments, the metallate precursor may be a tungstate or tungsten oxide, such as tungsten (IV) oxide, tungsten (VI) oxide, other tungsten oxides, or combinations of tungsten oxides. Examples of tungstates may include, but are not limited to ammonium metatungstate ($(NH_4)_6H_2W_{12}O_{40}$), tungstic acid, phosphotungstic acid, sodium tungstate, other tungstate precursor, or combinations of these. In some embodiments, the catalytically active compound precursor 134 may include a tungsten-containing compound that vaporizes or decomposes into a vapor containing tungsten at a temperature of from 150° C. to 1500° C. In some embodiments, the catalytically active compound precursor 134 may include at least one of tungsten metal, tungsten (IV) oxide, tungsten (VI) oxide, tungstic acid, tungstophosphoric acid, ammonium metatungstate, tungsten oxychloride, tungsten hexachloride, other tungsten-containing compounds, or combinations of these.

The catalytically active compound precursor may be continuously introduced to the source 132 of the catalytically active compound precursor vapor 136 in the second heating zone 130. The second heating zone 130 may be maintained at a temperature sufficient to vaporize the catalytically active compound precursor to generate the catalytically active compound precursor vapor 136 within the second heating zone 130. In some embodiments, the temperature of the second heating zone 130 may be maintained at a temperature sufficient to maintain a steady state of the catalytically active compound precursor vapor 136 in the second heating zone 130. In some embodiments, the second heating zone 130 may be maintained at a temperature of from 50° C. to 2000° C. so that a temperature of the catalytically active compound precursor vapor 136 in the second heating zone 130 is from 50° C. to 2000° C. For example, in some embodiments, the second heating zone 130 may be maintained at a temperature of from 50° C. to 1700° C., from 50° C. to 1450° C., from 300° C. to 2000° C., from 300° C. to 1700° C., from 300° C. to 1450° C., from 600° C. to 2000° C., from 600° C. to 1700° C., or from 600° C. to 1450° C. In other embodiments, the second heating zone 130 may be maintained at a temperature of from 600° C. to 1400° C., from 600° C. to 1350° C., from 600° C. to 1300° C., from 600° C. to 1200° C., from 600° C. to 1100° C., from 800° C. to 1450° C., from 800° C. to 1400° C., from 800° C. to 1350° C., from 800° C. to 1300° C., from 800° C. to 1200° C., from 800° C. to 1100° C., from 1000° C. to 1450° C., from 1000° C. to 1400° C., from 1000° C. to 1350° C., from 1000° C. to 1300° C., from 1000° C. to 1200° C., from 1100° C. to 1450° C., or from 1200° C. to 1450° C. In embodiments, the temperature of the second heating zone 130 may be controlled to control the vaporization rate of the catalytically active compound precursor 134.

In some embodiments, the second heating zone 130 may be operated at ambient pressure. Alternatively, the second heating zone 130 may also be operated at positive pressure or under a vacuum. A vapor pressure of the catalytically active compound precursor vapor 136 in the second heating zone 130 may be controlled by controlling the temperature of the second heating zone 130, the source 132 of the catalytically active compound precursor vapor 136, or both. The vapor pressure of the catalytically active compound precursor vapor 136 may also be controlled by controlling the flow rate of carrier gas 112 through the second heating zone 130. Thus, the aerosol processing method may not require that the vapor pressure of the catalytically active compound precursor 136 be maintained at a high level for an extended period of time through the application of a partial vacuum in the second heating zone 130.

In embodiments, the residence time of the catalyst support particles 114 in the second heating zone 130 may be sufficient to maintain steady state vaporization of the catalytically active compound precursor vapor 136 into the vapor phase in the second heating zone 130. For example, in some embodiments, the residence time of the catalyst support particles 114 in the second heating zone 130 may be sufficient to enable the catalytically active compound precursor 134 to vaporize uniformly from the source 132 and distribute through the second heating zone 130. In some embodiments, the residence time of the catalyst support particles 114 in the second heating zone 130 may be from 0.1 seconds to 10 seconds. In other embodiments, the residence time of the catalyst support particles 114 in the second heating zone 130 may be from 0.1 seconds to 9 seconds, from 0.1 seconds to 8 seconds, 0.1 second to 6 seconds, from 0.1 second to 4 seconds, from 0.5 seconds to 10 second, from 0.5 second to 9 seconds, from 0.5 seconds to 8 seconds, from 0.5 seconds to 6 seconds, from 0.1 second to 0.4 seconds, from 1 second to 10 seconds, from 1 second to 9 seconds, from 1 seconds to 8 second, from 1 second to 6 seconds, from 1 second to 4 seconds, from 2 seconds to 10 seconds, from 2 seconds to 9 seconds, from 2 seconds to 8 seconds, from 2 seconds to 6 seconds, or from 2 seconds to 4 seconds.

The catalyst support particles 114 may be contacted with the catalytically active compound precursor vapor 136 in the second heating zone 130. Upon exiting the second heating zone 130, the catalytically active compound precursor vapor 136 and the catalyst support particles 114 may be cooled. In some embodiments, the aerosolized flow of catalyst support particles 114 and catalytically active compound precursor vapor 136 may be cooled at a controlled rate to a temperature of less than 120° C., such as a temperature from 20° C. to 120° C. A desired cooling rate of the aerosolized flow of catalyst support particles 114 and catalytically active compound precursor vapor 136 may be achieved by modifying the residence time of the materials in the second heating zone 130 or by changing the distance between the second heating zone 130 and the separator 140. Additionally, the cooling rate of the aerosolized flow of catalyst support particles 114 and catalytically active compound precursor vapor 136 may be controlled using fans or heat exchangers or by changing the insulation materials. Further, the cooling rate of the aerosolized flow of catalyst support particles 114 and catalytically active compound precursor vapor 136 may be controlled by controlling a temperature of the separator 140.

As the catalytically active compound precursor vapor 136 cools, the catalytically active compound precursor vapor 136 may condense. As previously described, the catalytically active compound precursor vapor 136 may condense directly onto the surface of the catalyst support particles 114 or onto catalytically active compound previously condensed on the surface of the catalyst support particles 114. In some embodiments, the catalytically active compound precursor vapor 136 may condense on the outer surfaces of the catalyst support particles 114 and on surfaces of the catalyst support particles 114 that are accessible to gases and vapors, such as porous regions of the catalyst support particles 114 for example. Alternatively or additionally, the catalytically active compound precursor vapor 136 may condense onto itself (homogeneous nucleation) to create clusters or particles of catalytically active compound that may then diffuse to the catalyst support particles 114 and deposit onto the surface of the catalyst support particles 114. The clusters or particles of catalytically active compound may deposit onto the outer surfaces of the catalyst support particles 114 and on surfaces of the catalyst support particles 114 that are accessible to gases and vapors.

Condensation of the catalytically active compound precursor vapor 134 results in formation of the catalyst 101 having individual atoms, molecules, clusters, or particles of the catalytically active compound deposited on the catalyst support particles 114. The individual atoms, molecules, clusters, or particles of the catalytically active compound may be deposited on the surfaces of the catalyst support particles 114 that are accessible to the gases and vapors. For example, the catalytically active compound may be deposited on an outermost surface of the catalyst support particles 114, on the walls of pores in an outer portion of the catalyst support particles 114 in fluid communication with the outer surface of the catalyst support particles 114, or both. The interior portions of the catalyst support particles 114 may be substantially free of the catalytically active compound. As used in this disclosure, the term "substantially free" of a component means less than 0.1 wt. % of that component in a particular portion of a catalyst, stream, or reaction zone. For example, the interior portions of the catalyst support particles 114 may have less than 0.1 wt. % catalytically active compound, based on the total weight of the catalyst 101. The interior portions of the catalyst support particles 114 refers to the portions of the catalyst support particles 114 that are inaccessible to gases and vapors. For example, the interior of the catalyst support particles 114 includes the solid portions of the catalyst support particles 114 and internal pores of the catalyst support particles 114 that are not in fluid communication with the outer surface of the catalyst support particles 114.

In some embodiments, the resulting catalyst 101 particles may have 100% of the catalytically active compound deposited only on the surfaces of the catalyst support particles 114 that are accessible to vapors and gases, which may include the outermost surface of the catalyst support particles 114, walls of pores in an outer portion of the catalyst support particles 114 in fluid communication with the outer surface of the catalyst support particles 114, or both. The catalytically active compound may be deposited on enough of the surfaces of the catalyst support particles 114 that are accessible to vapors and gases to provide sufficient catalytic activity to the catalyst 101 particles. However, depositing the catalytically active compound over too great of a percentage of the surfaces of the catalyst support particles 114 that are accessible to vapors and gases may result in the catalytically active compound forming larger clusters or agglomerates, which may reduce the catalytic activity of the catalyst 101 particles. In some embodiments, the catalyst 101 particles may have the catalytically active compound deposited on greater than or equal to 1% of the surfaces of the catalyst support particles 114 that are accessible to vapors and gases, greater than or equal to 5% of the surfaces of the catalyst support particles 114 that are accessible to vapors and gases, greater than or equal to 10% of the surfaces of the catalyst support particles 114 that are accessible to vapors and gases, or even greater than or equal to 20% of the surfaces of the catalyst support particles 114 that are accessible to vapors and gases. In other embodiments, the catalyst 101 particles may have the catalytically active compound deposited on less than or equal to 50% of the surfaces of the catalyst support particles 114 that are accessible to vapors and gases, less than or equal to 40% of the surfaces of the catalyst support particles 114 that are accessible to vapors and gases, less than or equal to 30% of the surfaces of the catalyst support particles 114 that are accessible to vapors and gases, less than or equal to 20% of the surfaces of the catalyst support particles 114 that are accessible to vapors and gases, or even less than or equal to 10% of the surfaces of the catalyst support particles 114 that are accessible to vapors and gases. For example, in some embodiments the catalyst 101 particles may have the catalytically active compound deposited on from 1% to 50% of the surfaces of the catalyst support particles 114 that are accessible to vapors and gases, such as from 1% to 40%, from 1% to 30%, from 1% to 20%, from 1% to 10%, from 1% to 5%, from 5% to 50%, from 5% to 40%, from 5% to 30%, from 5% to 20%, from 5% to 10%, from 10% to 50%, from 10% to 40%, from 10% to 30%, from 10% to 20%, from 20% to 50%, from 20% to 40%, or from 20% to 30% of the surfaces of the catalyst support particles 114 that are accessible to vapors and gases.

The resulting catalyst 101 particles may have the catalytically active compound that is more dispersed, less clustered, or both, on the surfaces of the catalyst support particles 114 that are accessible to vapors and gases compared to conventional catalysts synthesized by wet impregnation methods or other similar methods. As used in this disclosure, the term "dispersed" refers to the catalytically active compound being spread out over the surfaces of the catalyst support particles 114 that are accessible to vapors and gases, as compared to being concentrated in larger clusters and agglomerates. For example, the "most-dispersed" state would comprise a mono-layer of molecules of the catalytically active compound deposited on the surfaces of the catalyst support particles 114.

The degree to which the catalytically active compound is dispersed on the surfaces of the catalyst support particles 114 accessible to vapors and gases may be evaluated by determining the average particle size of the catalytically active compound deposited on surfaces of the catalyst support particles 114. The average particle size of the catalytically active compound may be determined using Small Angle X-Ray Scattering (SAXS) as subsequently discussed in this disclosure. As used in this disclosure in relation to the catalytically active compound deposited on surfaces of the catalyst support particles accessible to vapors and gases, the "average particle size" refers to an average radius of the crystals, clusters, or agglomerates, of the catalytically active compound deposited on the surfaces of the catalyst support particles accessible to vapors and gases. The average particle size includes the radii of single atoms and single molecules of the catalytically active compound deposited as single atoms or single molecules on the surfaces of the catalyst support particles. In general, the smaller the average particle size of the catalytically active compound deposited on the surfaces of the catalyst support particles 114 the more dispersed the catalytically active compound is and the less clustered the catalytically active compound is. Greater average particle size of the catalytically active compound indicates that the deposition process has resulted in additional clustering or agglomeration of the catalytically active compound into larger-sized crystals, clusters, or agglomerates, which may reduce the degree to which the catalytically active compound is dispersed on the surfaces of the catalyst support particles 114 that are accessible to vapors and gases.

In some embodiments, the average particle size of the catalytically active compound deposited on the surfaces of the catalyst support particles 114 that are accessible to vapors and gases may be less than the average particle size of the catalytically active compound deposited on the catalyst support particles 114 by wet impregnation or other conventional process. For example, in some embodiments, the average particle size (average radius) of the catalytically active compound deposited on the surfaces of the catalyst support particles 114 that are accessible to vapors and gases may be less than or equal to 2.5 nanometers (nm), less than or equal to 2 nm, less than or equal to 1.5 nm, or less than or equal to 1 nm. In other embodiments, the average particle size of the catalytically active compound deposited on the surface of the catalyst support particles 114 that is accessible to vapors and gases may be greater than or equal to an atomic radius of a single atom of the catalytically active compound or greater than or equal to a molecular radius of a single molecule of the catalytically active compound. In some embodiments, the average particle size of the catalytically active compound deposited on the surfaces of the catalyst support particles 114 that are accessible to vapors and gases may be from 0.1 nm to 2.5 nm, from 0.1 nm to 2 nm, from 0.1 nm to 1.5 nm, from 0.1 nm to 1 nm, from 0.1 nm to 0.5 nm, from 0.5 nm to 2.5 nm, from 0.5 nm to 2 nm, from 0.5 nm to 1.5 nm, from 0.5 nm to 1 nm, from 1 nm to 2.5 nm, from 1 nm to 2 nm, or from 1 nm to 1.5 nm.

The average crystalline size of the catalytically active compound may be determined using the SAXS method to measure the average radius of the catalytically active compound crystals and/or agglomerates using a Bruker NANO-STAR™ small angle X-ray scattering system with the x-ray source operating at 45 kilovolts (kV) and 650 microangtroms (µA). Samples are placed in quartz capillary tubes having an outer diameter of 1.5 millimeter (mm), a length of 80 mm length, and a wall thickness of 0.01 mm. Quartz capillary tubes may be obtained from the Charles Supper Co., of Natick, Mass., USA. After placing the samples in the capillary tubes, the capillary tubes are sealed with CRYTOSEAL™, available from Fisher Scientific, Fairlawn, N.J., USA, and hot-melt adhesive available from Ted Pella, Redding, Calif., USA. Each sealed quartz capillary tube is placed in a sample mount that orients the capillary tube in the sample chamber upright and perpendicular to the beam. The sample chamber is placed under vacuum to eliminate parasitic scattering from air. Two-dimensional intensity data are collected by averaging the scattered X-ray intensity over a 30 minute window.

Intensity patterns are azimuthally averaged and corrected for background and indirect transmission using the appropriate blank and control sample data and assuming a glassy carbon transmission value of 0.1400. Scattering data curves are initially fit using a Porod analysis to provide a first approximation of the particle size. Direct fitting is then performed using the Bruker Diffrac.SAXS software over a q range of from 0.1357 per angstrom ($Å^{-1}$) to 0.30154 $Å^{-1}$ and employing a theoretical scattering function for polydisperse spheres. The size and size distribution of the particles is determined assuming a lognormal distribution of core radii assuming no relevant interactions between the particles. Direct modelling results are replicated via three separate blind, independent fits, and the extremity results from these fits are used to generate the reported ranges for particle radius. The SAXS method is further described in Wojciech, Szczerba et al., "SAXS Analysis of Single- and Multi-Core Iron Oxide Magnetic Nanoparticles," J Appl Crystallogr. 2017 Apr. 1; 50(Pt 2): 481-488 (Published online 2017 Mar. 14). It is understood that other methods and technologies may be used to determine the average particle size of the catalytically active compound.

Figure 8:
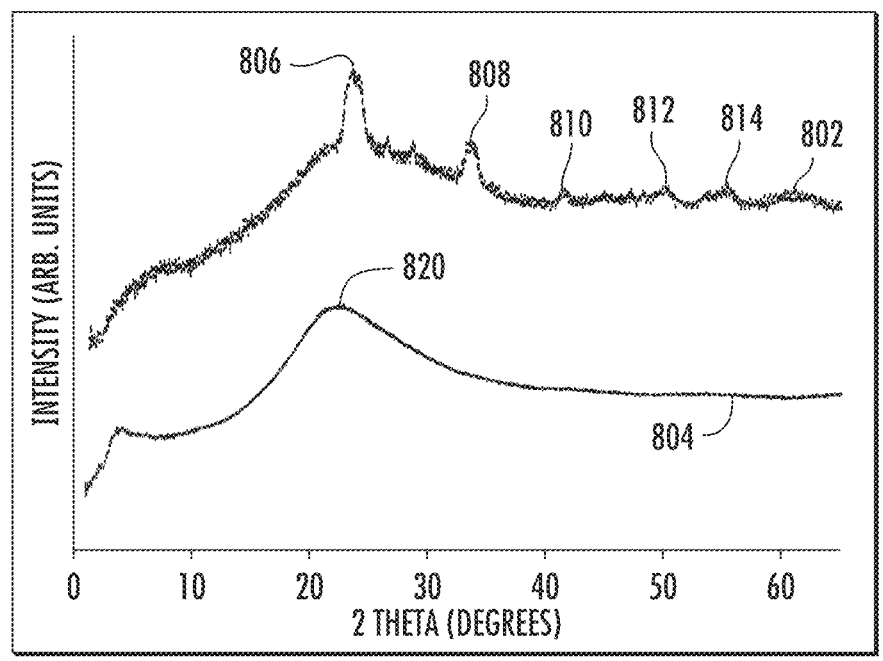
FIG. 8 is a XRD graph illustrating the XRD profile of the metathesis catalyst made by the process of FIG. 1, in accordance with one or more embodiments of the present disclosure, compared to the XRD profile of a metathesis catalyst made by conventional wet impregnation processes.

Alternatively, the degree to which the catalytically active compound is dispersed on the surfaces of the catalyst support particles 114 that are accessible to vapors and gases may be evaluated by analyzing the X-Ray Diffraction (XRD) pattern of the catalyst 101 particles. Referring to FIG. 8, the XRD pattern 802 is shown for a conventional wet impregnated catalyst having tungsten oxide as the catalytically active compound deposited on the surface of the catalyst support particles by a wet impregnation method. As shown in FIG. 8, the XRD pattern 802 for the conventional wet impregnated catalyst exhibits a background peak with a major peak 806 at 2 theta (2θ) equal to about 22 degrees)(° and several secondary peaks 808, 810, 812, and 814 from about 2θ=30° to about 2θ=60°. As used in this disclosure, the term "major peak" of the XRD pattern refers to the peak having the greatest intensity compared to one or more "secondary peaks" having intensities less than the major peak. The peaks 806, 808, 810, 812, and 814 indicate crystallinity of the tungsten oxide catalytically active compound on the surface of the conventional wet impregnated catalyst. The crystallinity indicates that the tungsten oxide catalytically active compound may be forming increasingly larger clusters and crystals on the surface of the catalyst support particle 114.

FIG. 8 also shows the XRD pattern 804 for the catalyst 101 having tungsten oxide as the catalytically active compound deposited onto the catalyst support particle 114 by the aerosol processing methods described in this disclosure. The XRD pattern 804 for the catalyst 101 made by aerosol processing exhibits a single broad signature peak 820 at about 2θ=22 degrees. As previously described, the single broad signature peak (major peak) at about 2θ=22 degrees is indicative of amorphous materials. However, in contrast to the XRD pattern 802 for conventional wet impregnation catalyst previously described, the XRD pattern 804 for the catalyst 101 prepared by the aerosol processing method does not exhibit the secondary peaks at 2θ greater than 30 degrees. The XRD pattern 804 for catalyst 101 exhibits a single signature peak 820 and does not include one or more secondary peaks. Thus, the XRD pattern 804 does not indicate any degree of crystallinity of either the support material or the tungsten oxide catalytically active compound. This indicates that the level of crystallinity of the catalyst 101 prepared by aerosol processing methods is nonexistent compared to the level of crystallinity of the conventional wet impregnation catalyst and cannot be detected with XRD beyond the broad amorphous peak of the catalyst support material. The presence of secondary peaks in the XRD pattern for a catalyst indicates a greater crystallinity of the catalytically active compound and a lesser degree to which the catalytically active compound is dispersed on the surface of the catalyst support particles 114. In some embodiments, the catalyst 101 may have an XRD pattern that lacks secondary peaks. In some embodiments, the catalyst 101 may have an X-Ray Diffraction pattern consisting of the single signature peak 820 within a range of 2θ=15 degrees to 2θ=60 degrees. This signature peak 820 is an amorphous signature and is not due to any crystallinity in the catalyst 101.

Condensation of the catalytically active compound precursor vapor 136 may occur through a decrease in the temperature of the catalytically active compound precursor vapor 136 resulting from cooling as catalyst support particles 114 and the catalytically active compound precursor vapor 136 exit the second heating zone 130. The carrier gas 112 flowrate may influence the rate of cooling of the catalytically active compound precursor vapor 136 and thus the rate of condensation. In some embodiments, the carrier gas 112 flowrate may be controlled to control the cooling rate of the catalytically active compound precursor vapor 136. Additionally, a curvature of the catalyst support particle 114 or clusters or nanoparticles of the catalytically active compound may depress the vapor pressure of the catalytically active compound precursor vapor 136 locally in the vicinity of the catalyst support particle 114 or clusters/nanoparticles of the catalytically active compound, thereby causing condensation of the catalytically active compound precursor vapor 136 at higher temperatures compared to condensation resulting from cooling. Thus, condensation of the catalytically active compound precursor vapor 136 may occur at the higher temperatures within the second heating zone 130 before the catalytically active compound precursor vapor 136 exits the second heating zone 130.

The amount of the catalytically active compound condensed onto the surfaces of the catalyst support particles 114 may be controlled by controlling the concentration of the catalyst support material 114, the selection of and temperature of the catalytically active compound precursor in the second heating zone 130, such as by controlling the temperature of the second heating zone 130, the temperature of the source 132 of the catalytically active compound precursor, or both. Controlling the temperature of the second heating zone 130, source 132, or both influences the vaporization rate of the catalytically active compound precursor. The amount of catalytically active compound condensed onto the surfaces of the catalyst support particles 114 may also be controlled by controlling the flowrate of the aerosol 113 through the second heating zone 130, the concentration of the catalyst support precursor 104 in the catalyst support precursor mixture 108, the particle size of the catalyst support particles 114, the temperature of the aerosol 113 during deposition, and the final temperature of the aerosol at the separator 140, the concentration of the catalyst support particles 114 in the aerosol 113, or combinations of these.

The deposition rate of the catalytically active compound onto the surfaces of the catalyst support particles may also be controlled by controlling the temperature of the catalytically active compound precursor in the second heating zone 130, the position of the source 132 of the catalytically active compound precursor within the second heating zone 130, the flowrate of the aerosol 113 through the aerosol processing system 100, the concentration of the catalyst support precursor 104 in the catalyst support precursor mixture 108, the cooling rate at the exit of the second heating zone 130, the concentration of the catalyst support particles 114 in the aerosol 113, the particle size of the catalyst support particles 114 in the aerosol 113, or combinations of these.

In some embodiments, the catalytically active compound precursor 134 may be a gas that may decompose in the second heating zone 130 to deposit the catalytically active compound onto the surfaces of the catalyst support particles 114. In these embodiments, the catalytically active compound precursor gas may be introduced directly to the second heating zone 130. Heat from the second heating zone 130 may cause the catalytically active compound precursor gas to decompose to produce the catalytically active compound, which may then be deposited on the surfaces of the catalyst support particles 114.

The catalyst 101 may have an amount of the catalytically active compound deposited on the surface of the catalyst 101 sufficient to provide a desired level of catalytic activity to the catalyst 101. In some embodiments, the catalyst 101 may have from 0.0002 wt. % to 20 wt. % catalytically active compound, based on the total weight of the catalyst 101 particles. In other embodiments, the catalyst 101 may have from 0.0002 wt. % to 10 wt. %, from 0.0002 wt. % to 5 wt. %, from 0.0002 wt. % to 1 wt. %, from 0.0002 wt. % to 0.5 wt. %, from 0.001 wt. % to 20 wt. %, from 0.001 wt. % to 10 wt. %, from 0.001 wt. % to 5 wt. %, from 0.001 wt. % to 1 wt. %, from 0.001 wt. % to 0.5 wt. %, from 0.01 wt. % to 20 wt. %, from 0.01 wt. % to 10 wt. %, from 0.01 wt. % to 5 wt. %, from 0.01 wt. % to 1 wt. %, from 0.01 wt. % to 0.5 wt. %, from 0.1 wt. % to 20 wt. %, from 0.1 wt. % to 10 wt. %, from 0.1 wt. % to 5 wt. %, from 0.1 wt. % to 1 wt. %, from 0.1 wt. % to 0.5 wt. %, from 0.5 wt. % to 20 wt. %, from 0.5 wt. % to 10 wt. %, from 0.5 wt. % to 5 wt. %, from 0.5 wt. % to 1 wt. %, from 1 wt. % to 20 wt. %, from 1 wt. % to 10 wt. %, or from 1 wt. % to 5 wt. % catalytically active compound, based on the total weight of the catalyst. In some embodiments, the catalyst 101 may have less than or equal to 10 wt. %, less than or equal to 5 wt. %, less than or equal to 1 wt. %, less than or equal to 0.5 wt. %, or even less than or equal to 0.4 wt. % catalytically active compound, based on the total weight of the catalyst 101 particles.

In embodiments, the aerosol processing system 100 includes the separator 140 for separating the catalyst 101 from the carrier gas 112 and collecting the catalyst 101. The carrier gas 112 and the catalyst 101 particles entrained in the carrier gas 112 pass out of the second heating zone 120 and into the separator 140. The method of synthesizing the catalyst 101 includes separating the catalyst 101 from the carrier gas 112 and collecting the catalyst 101. In some embodiments, the carrier gas 112 may be passed from the separator 140 to the atmosphere without further treatment. Alternatively, the carrier gas 112 exiting the separator may be further processed to recover residual constituents of the process, such as catalytically active compound precursor vapors 136, organic solvents from the catalyst support precursor mixture, or other contaminants, for example. In some embodiments, the carrier gas 112 passed out of the separator 140 is substantially free of chlorine-containing compounds. As an example, the carrier gas 112 exiting the separator 140 may have less than 0.1 wt. % chlorine-containing compounds.

In some embodiments, the separator 140 may be a cyclone separator, an electrostatic precipitator, or a filter that is used to separate the catalyst 101 from the flow of the carrier gas 112 exiting the second heating zone 130. An example filter may comprise borosilicate fibers bound with polyvinylidene fluoride (PVDF) configured to have a desired efficiency at capturing 0.01 micron (μm) particles. Another example filter may consist of quartz bound with an inorganic resin that can tolerate higher operating temperatures. The filter may also be comprised of any commercially available bag house filter material. In selecting a filter, there is a desire to balance pore size of the filter to sufficiently collect the catalyst 101 particles with the resulting pressure increase which results as the filter collects catalyst 101 particles and at temperatures suitable for collection. As the filter begins to clog and a particle cake forms, the filter becomes a more efficient filter and the pressure starts to rise. In operation, the resulting pressure rise may be used as an indicator of the quantity of catalyst 101 collected within the filter. Additionally, the filter material may be temperature stable at temperatures greater than or equal to the temperature of the aerosol 113 exiting the second heating zone 130 to prevent the filter material from undergoing combustion.

As described above, FIG. 1 illustrates vaporization of the catalytically active compound precursor 134 by positioning the source 132 of the catalytically active compound precursor 134 in the second heating zone 130 and vaporizing the catalytically active compound precursor 134 in the second heating zone 130. Alternatively, as shown in FIGS. 2-6, other embodiments of aerosol processing systems may utilize alternative methods of providing the catalytically active compound precursor 134 or catalytically active compound to the second heating zone 130.

Figure 2:
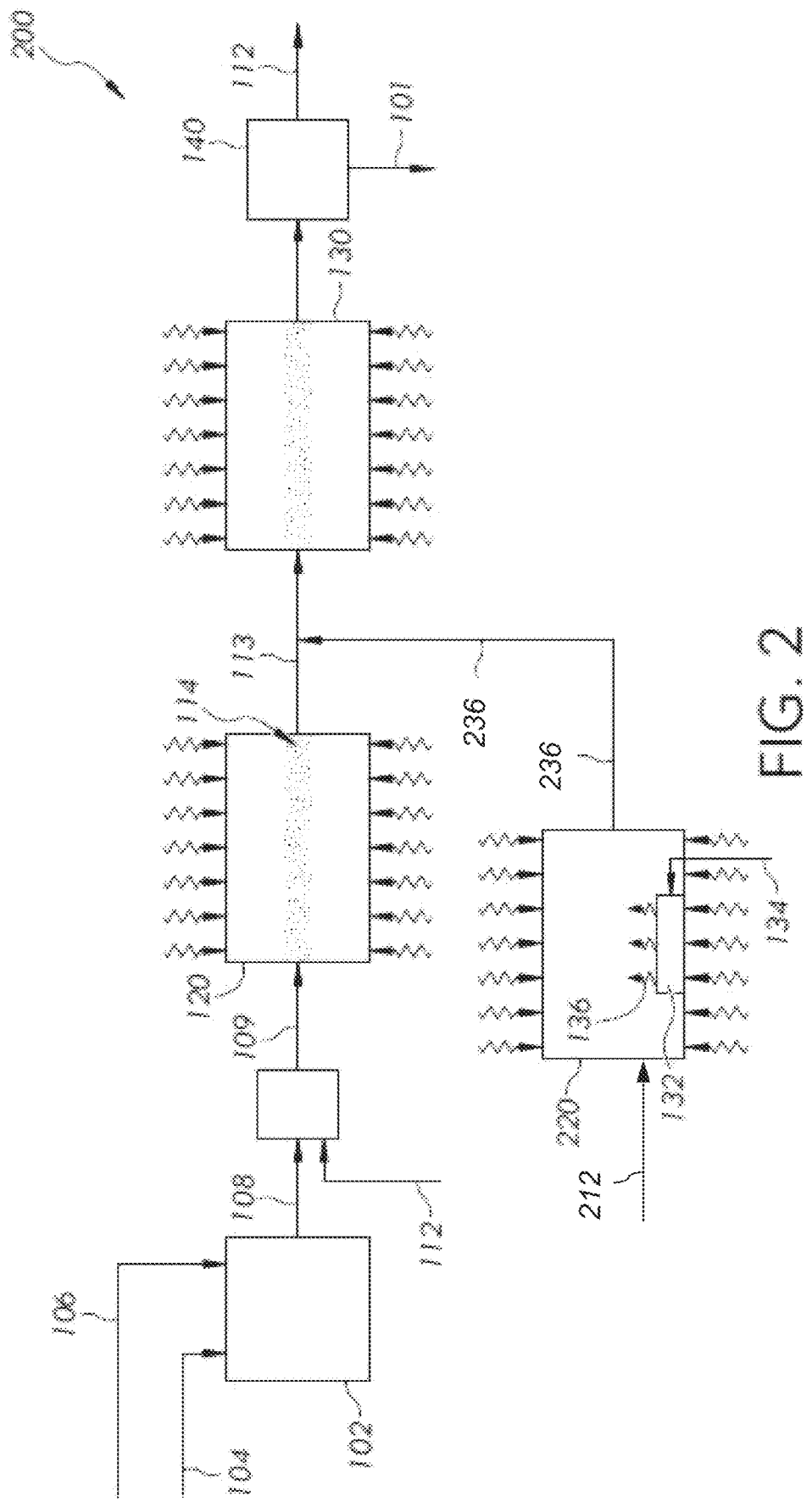
FIG. 2 schematically depicts another aerosol processing system, in accordance with one or more embodiments of the present disclosure.

Referring now to FIG. 2, an aerosol processing system 200 may include a third heating zone 220, and the source 132 of the catalytically active compound precursor vapor 136 may be positioned within the third heating zone 220. The aerosol processing system 200 may also include the vessel 102, the aerosolizing unit 110, the first heating zone 120, the second heating zone 130, and the separator 140 previously described for the aerosol processing system 100 of FIG. 1. As shown in FIG. 2, the third heating zone 220 of aerosol processing system 200 may be parallel to the first heating zone 120 and may be upstream of the second heating zone 130. In some embodiments, the third heating zone 220 may be a third furnace, more specifically, a region in a third furnace.

In FIG. 2, the source 132 of the catalytically active compound precursor vapor 136 may include a crucible or other open vessel containing a catalytically active compound precursor. Heat from the third heating zone 220 may be transferred to the source 132 and the catalytically active compound precursor contained within the source 132. The heat from the third heating zone 220 may cause the catalytically active compound precursor to vaporize to form the catalytically active compound precursor vapor 136. Alternatively, in some embodiments, the source 132 may be heated independently of the third heating zone 220. The catalytically active compound precursor may transfer/vaporize into the vapor phase through evaporation, sublimation, reaction/decomposition, melting, or combinations of these, for example. In embodiments, a catalytically active compound precursor stream 134 comprising the catalytically active compound precursor may be continuously or periodically introduced to the source 132 to maintain continuous generation of the catalytically active compound precursor vapor 136 in the third heating zone 220.

A carrier gas 212 may be introduced to the third heating zone 220 to carry the catalytically active compound precursor vapor 136 to the second heating zone 130. The carrier gas 212 may be any of the carrier gases previously described for carrier gas 112. The carrier gas 212 may be the same as carrier gas 112 or different than carrier gas 112. Stream 236 may include the catalytically active compound precursor vapor 136 carried by the carrier gas 212 and may be passed out of the third heating zone 220. In some embodiments, the stream 236 may be combined with the aerosol 113 passing out of the first heating zone 120 upstream of the second heating zone 130. In these embodiments, the aerosol 113 and the stream 236 are mixed and the catalytically active compound precursor vapor 136 in stream 236 and the aerosol 113 are contacted before being passed to the second heating zone 130. Alternatively, the aerosol 113 and the stream 236 may be individually passed to the second heating zone 130. In these embodiments, the aerosol 113 and the catalytically active compound precursor vapor 136 in stream 236 are mixed and contacted in the second heating zone 130. Upon exiting the second heating zone 130, the catalytically active compound precursor vapor 136 condenses as previously described in this disclosure to produce the catalyst 101 having the catalytically active compound deposited on the surfaces of the catalyst 101.

Alternatively, in some embodiments, the stream 236 may be cooled upon exiting the third heating zone 220 to produce nanoparticles of the catalytically active compound from the catalytically active compound precursor vapor 136 in the stream 236. The catalytically active compound nanoparticles may then be combined with the aerosol 113. The catalytically active compound nanoparticles may collide with the catalyst support particles 114 of aerosol 113 in the second heating zone 130 to form the catalyst 101 comprising the catalytically active compound nanoparticles deposited on the surfaces of the catalyst 101.

Figure 3:
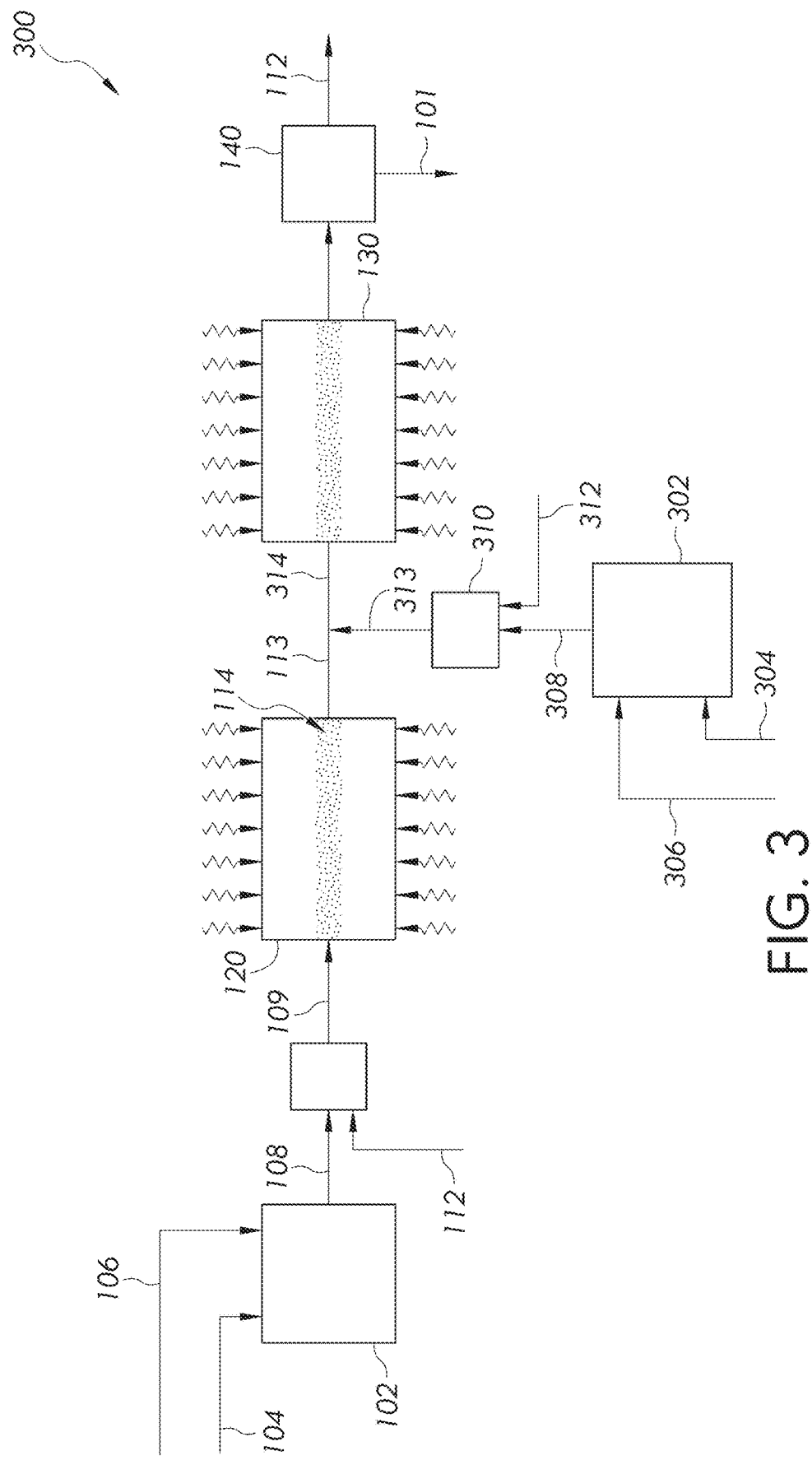
FIG. 3 schematically depicts yet another aerosol processing system, in accordance with one or more embodiments of the present disclosure.
Figure 4:
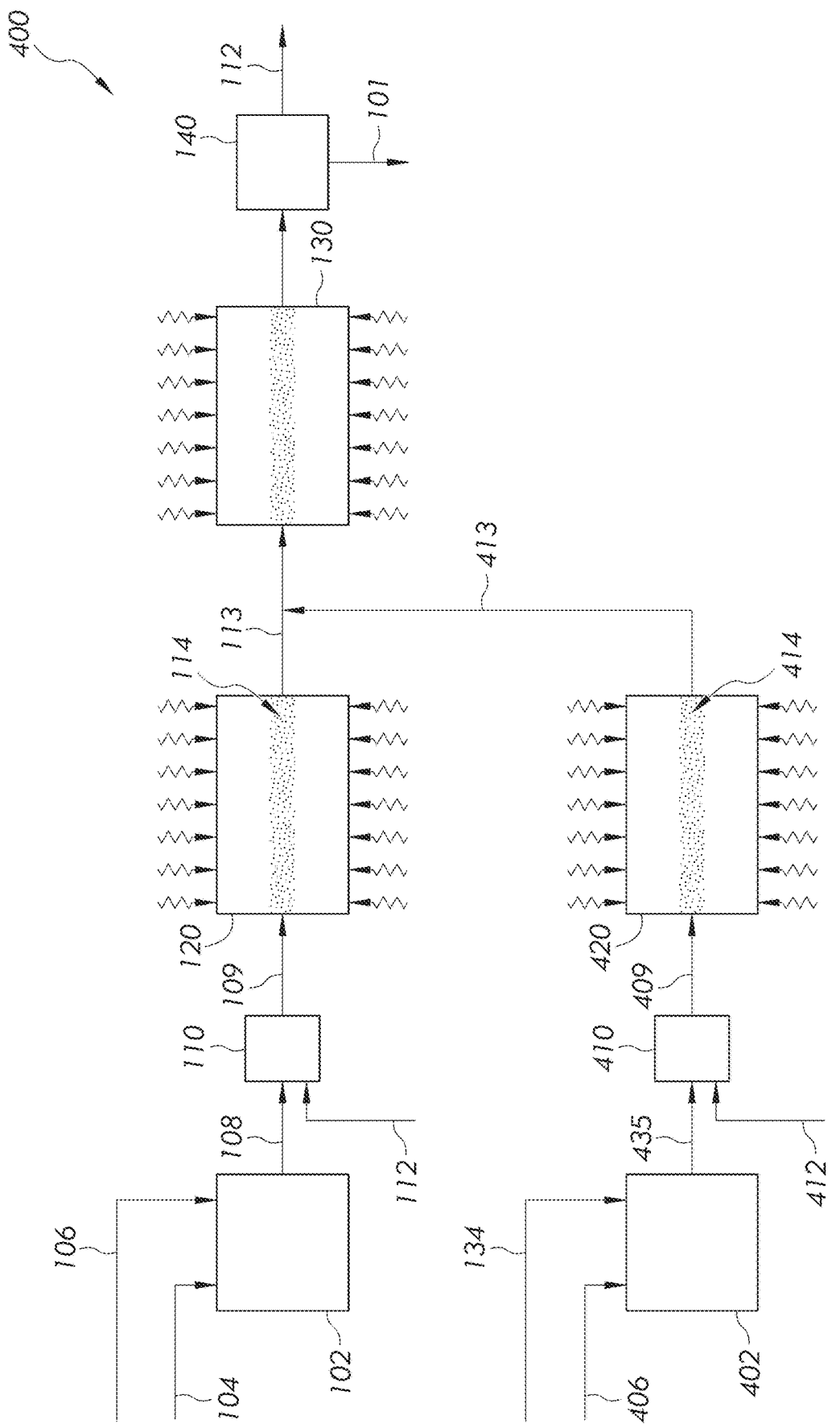
FIG. 4 schematically depicts still another aerosol processing system, in accordance with one or more embodiments of the present disclosure.
Figure 5:
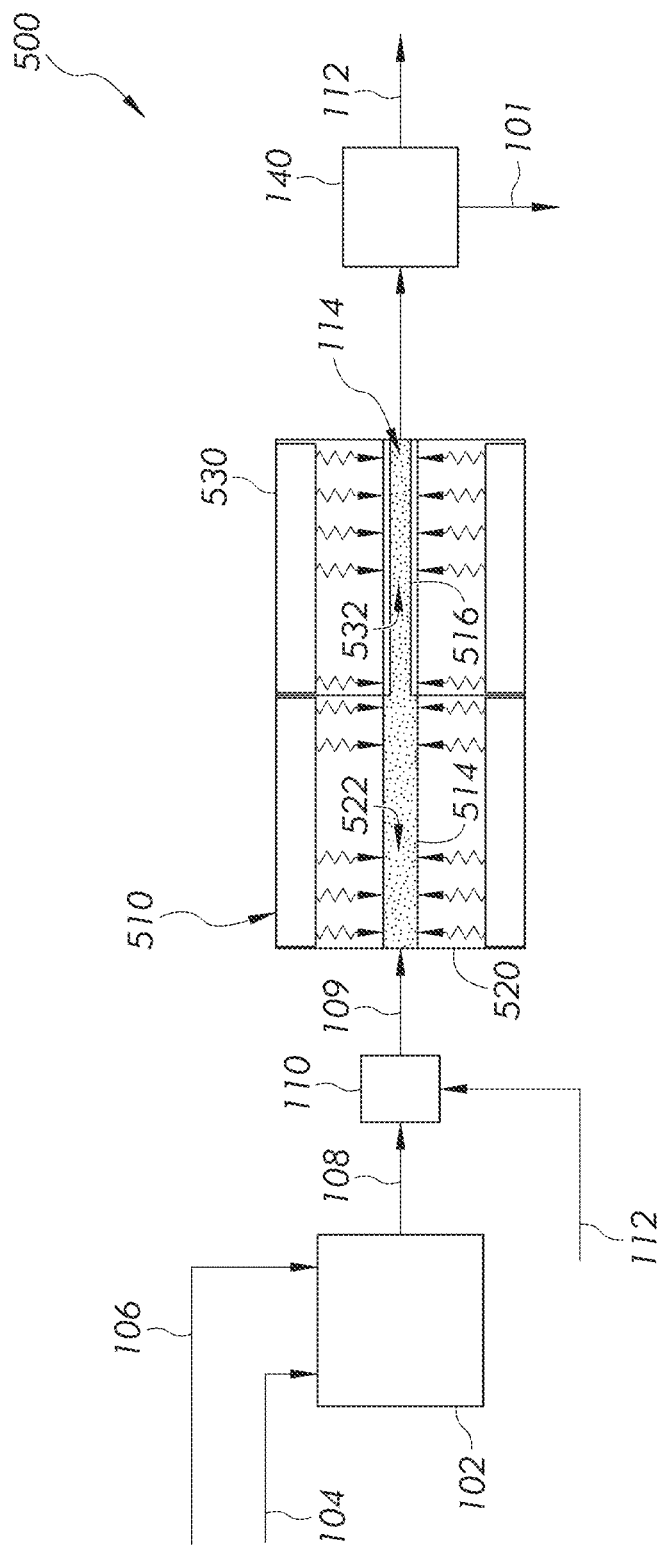
FIG. 5 schematically depicts still another aerosol processing system, in accordance with one or more embodiments of the present disclosure.

Referring to FIG. 3, in other embodiments, an aerosol processing system 300 may include a supplemental vessel 302 and a supplemental aerosolizing unit 310. The aerosol processing system 300 also includes the vessel 102, the aerosolizing unit 110, the first heating zone 120, the second heating zone 130, and the separator 140 previously described in relation to aerosol processing system 100 of FIG. 1. In the aerosol processing system 300 of FIG. 3, the catalytically active compound precursor 304 may be combined with a diluent 306 in the supplemental vessel 302 to produce a catalytically active compound precursor mixture 308. The catalytically active compound precursor 304 may include any of the materials previously described in relation to catalytically active compound precursors. Additionally, the supplemental diluent 306 and the supplemental carrier gas 312 may be any of the material described above relative to diluent 106 and carrier gas 312, respectively.

Figure 6:
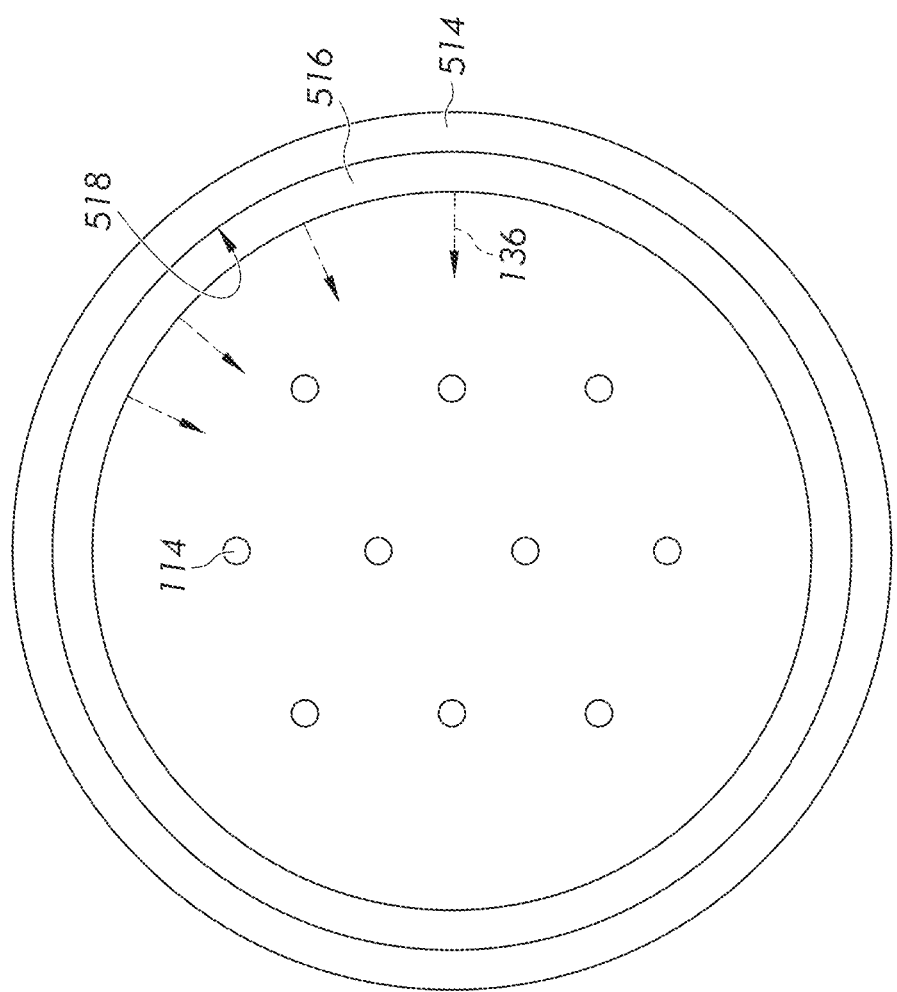
FIG. 6 is a cross-section of a reaction tube of the aerosol processing system of FIG. 5, in accordance with one or more embodiments of the present disclosure.

The catalytically active compound precursor mixture 308 may be passed to the supplemental aerosolizing unit 310. The supplemental aerosolizing unit 310 may be any of the devices previously described in relation to aerosolizing unit 110. The supplemental aerosolizing unit 310 may aerosolize the catalytically active compound precursor mixture 308 with a supplemental carrier gas 312 to produce a catalyst precursor aerosol 313 comprising droplets of the aerosolized catalytically active compound precursor mixture 308 and the supplemental carrier gas 312. In some embodiments, the catalyst precursor aerosol 313 may be combined with the aerosol 113 passing out of the first heating zone 120 to form combined aerosol stream 314 upstream of the second heating zone 130, as shown in FIG. 3. The combined aerosol stream 314 may then be passed to the second heating zone 220. Alternatively, in other embodiments, the catalyst precursor aerosol 313 and the aerosol 113 may be independently passed to the second heating zone 120 and then combined in the second heating zone 120. The catalyst precursor aerosol 313 may react, dry, or both in the second heating zone 130 to form a plurality of solid particles of the catalytically active compound, and the plurality of solid particles of the catalytically active compound may then collide with the aerosol 113 and deposit onto aerosol 113 to form the catalyst 101. Additionally, the catalyst precursor aerosol 313 may collide with aerosol 113 prior to reacting, drying, or both to form a combined aerosol stream 314 that contains both solid and liquid material. When introduced into the second heating zone 130, the greater temperature in the second heating zone 130 may cause the catalyst precursor aerosol 313 to react, dry, or both on and around catalyst support particles 114 of aerosol 113 to produce the catalyst 101.

Referring to FIG. 4, an aerosol processing system 400 is depicted that includes the vessel 102, the aerosolizing unit 110, the first heating zone 120, the second heating zone 130, and the separator 140 previously described in relation to the aerosol processing system 100 of FIG. 1. As shown in FIG. 4, the aerosol processing system 400 may further include a supplemental vessel 402, a supplemental aerosolizing unit 410 positioned downstream of the supplemental vessel 402, and a third heating zone 420 downstream of the supplemental aerosolizing unit 410. The supplemental vessel 402, the supplemental aerosolizing unit 410, and the third heating zone 420 may be parallel to the vessel 102, aerosolizing unit 110, and first heating zone 120. The catalytically active compound precursor 134 may be combined with a supplemental diluent 406 in the supplemental vessel 402 to produce a catalytically active compound precursor mixture 435. The supplemental diluent 406 may be any of the materials previously described for diluent 106.

The catalytically active compound precursor mixture 435 and a supplemental carrier gas 412 may be introduced to the supplemental aerosolizing unit 410. The supplemental carrier gas 412 may be any of the materials previously described for carrier gas 112. In some embodiments, the supplemental carrier gas 412 may be the same material as the carrier gas 112. The catalytically active compound precursor mixture 435 may be aerosolized in the supplemental aerosolizing unit 410 to produce a catalytically active compound precursor aerosol 409 comprising droplets of the catalytically active compound precursor mixture 435 and the supplemental carrier gas 412. The catalytically active compound precursor aerosol 409 may be passed to and through the third heating zone 420. In the third heating zone 420, the catalytically active compound precursor aerosol 409 may dry, react, or decompose to produce a plurality of catalytically active compound particles 414 aerosolized in the supplemental carrier gas 412. Aerosol 413 may comprise the catalytically active compound particles 414 aerosolized in the supplemental carrier gas 412.

The aerosol 413 may be combined with the aerosol 113 upstream of the second heating zone 130 or in the second heating zone 130. The catalytically active compound particles 414 of aerosol 413 may contact the catalyst support particles 114 of aerosol 113 in the second heating zone 130, which may cause the catalytically active compound particles 414 to deposit onto the surfaces of the catalyst support particles 114 to produce the catalyst 101. Thus, the catalytically active compound particles 414 and the catalyst support particles 114 are formed independently and then combined to deposit the catalytically active compound particles 414 on the surfaces of the catalyst support particles 114.

Referring now to FIG. 5, another alternative aerosol processing system 500 for synthesizing the catalyst 101 is depicted. The aerosol processing system 500 of FIG. 5 may include the vessel 102 for preparing the catalyst support precursor mixture 108 from the catalyst support precursor 104, diluent 106, and optionally a dopant. The aerosol processing system 500 may further comprise the aerosolizing unit 110 and a continuous aerosol flow synthesis reactor 510. The continuous aerosol flow synthesis reactor 510 may include a reaction tube 514. The reaction tube 514 may extend through one or a plurality of heating elements, such as a first furnace 520 and a second furnace 530, for example. Other heating elements, such as resistance heating elements and the like, are envisioned for heating sections of the reaction tube 514. A portion of the reaction tube 514 may be seasoned with a catalytically active precursor. As used in this disclosure, the term "season" refers to a process of pretreating the reaction tube 514 of aerosol flow synthesis reactor 510 with a catalytically active compound precursor vapor 136 (FIG. 6) to deposit a layer 516 of a catalytically active compound precursor on an inner surface 518 (FIG. 6) of the reaction tube 514. FIG. 6 illustrates a cross section of the reaction tube 514 having the layer 516 of catalytically active compound precursor deposited on the inner surface 518 of the reaction tube 514. Referring back to FIG. 5, in some embodiments, the reaction tube 514 may include at least a first heating zone 522 and a second heating zone 532, and the layer 516 of catalytically active compound precursor may be deposited on the inner surface 518 of the reaction tube 514 in the second heating zone 532 of the reaction tube 514.

Referring to FIGS. 5 and 6, in operation, the catalyst support precursor 104 and the diluent 106, plus any optional dopants, are combined and mixed in the vessel 102 to form the catalyst support precursor mixture 108. The catalyst support precursor mixture 108 is then passed to the continuous aerosol flow synthesis reactor 510. In the continuous aerosol flow synthesis reactor 510, the catalyst support precursor mixture 108 is aerosolized to form the aerosolized catalyst support precursor mixture 109, which comprises a plurality of droplets of the catalyst support precursor mixture 108 dispersed in a carrier gas 112. The carrier gas 112 entrains the droplets of the aerosolized catalyst support precursor mixture 109 and conveys the aerosolized catalyst support precursor mixture 109 through the reaction tube 514 of the continuous aerosol flow synthesis reactor 510. In the first heating zone 522, the reaction tube 514 is heated. The heat dries the diluent from the droplets of the aerosolized catalyst support precursor mixture 109, reacts the catalyst support precursors 104, or both to form the catalyst support particles 114. The catalyst support particles 114 are conveyed by the carrier gas 112 through the second heating zone 532. The second heating zone 532 is heated to cause the catalytically active compound precursor in the layer 516 of catalytically active compound precursor to vaporize to form the catalytically active compound precursor vapor 136 (FIG. 6). The catalytically active compound precursor vapor 136 distributes throughout the second heating zone 532 of the reaction tube 514. The catalyst support particles 114 carried by the carrier gas pass through the second heating zone 532 where the catalyst support particles 114 contact the catalytically active compound precursor vapor 136. The catalytically active compound precursor vapor 136 condenses on the surfaces of the catalyst support particles 114 to form the catalyst 101 comprising a layer of the catalytically active compound deposited on the catalyst support particles 114. The catalyst 101 may then be separated from the carrier gas 112 in the separator 140 downstream of the continuous aerosol flow synthesis reactor 210.

The method of producing the catalyst may include seasoning the reaction tube 514 extending through the second furnace with the catalytically active compound precursor. Seasoning the reaction tube 514 may comprise vaporizing the catalytically active compound precursor to form a catalytically active compound precursor vapor and condensing the catalytically active compound precursor vapor onto an inner surface 518 of the reaction tube 514 to form a layer 516 of the catalytically active compound precursor on the inner surface 518 of the reaction tube 514. The method may further include heating the reaction tube 514 to re-vaporize the catalytically active compound precursor from the inner surface 518 of the reaction tube 514 to produce the catalytically active compound precursor vapor 136, passing the plurality of catalyst support particles 114 through the reaction tube 514 where the plurality of catalyst support particles 114 contact the catalytically active compound precursor vapor 136, and condensing the catalytically active compound precursor vapor 136 on the surfaces of the catalyst support particles 114.

As previously discussed in relation to FIGS. 1-5, the catalysts 101 formed by the aerosol processing methods have individual atom molecules, clusters, or particles of the catalytically active compound deposited on the surfaces of the catalyst support particles 114. When deposited using the aerosol processing methods, this layer of catalytically active compounds is concentrated at the surfaces of the catalyst support particles 114 that are accessible to gaseous reactants rather than being fully or at least partially embedded in the catalyst support particles 114. Thus, the catalytically active compounds deposited on the surface of the catalyst support particles 114 are highly active compared to conventionally prepared catalysts. This enables the catalyst 101 formed using the aerosol processing methods to have less of the catalytically active compound but provide equivalent or increased catalytic activity relative to conventionally prepared catalysts, such as catalysts prepared by wet impregnation for example. In some embodiments, the catalyst 101 formed using the aerosol processing methods may have less than or equal to 50% of catalytically active compound compared to conventionally prepared catalysts having the catalytically active compound distributed throughout the catalyst support particle. In other embodiments, the catalyst 101 formed using the aerosol processing methods may have less than or equal to 25%, or less than or equal to 20%, or less than or equal to 15%, or less than or equal to 10% of the catalytically active compound compared to conventionally prepared catalysts having the catalytically active compound distributed throughout the catalyst support particle.

Reducing the amount of the catalytically active compounds in the catalyst 101 may reduce the cost of the catalyst 101, particularly when using costly catalytically active compounds such as platinum, gold, or palladium for example, relative to conventionally prepared catalysts. Additionally, the aerosol processing method of forming the catalysts 101 enables continuous production of the catalysts. The aerosol processing system and methods described in this disclosure may enable greater control of the deposition rate and total amount of the catalytically active compound deposited on the surfaces of the catalyst support particles 114, which may enable control of the catalytic activity of the catalyst. The aerosol processing method may enable fine tuning of the catalytic activity of a catalyst for a specific application. Isomerization, metathesis, and isomerization and metathesis catalysts produced using the aerosol processing methods may result in less coke formation on the catalyst during metathesis reactions, which may lead to longer catalyst life.

In one example implementation, the aerosol process methods previously discussed may be used to synthesize an isomerization catalyst, metathesis catalyst, or an isomerization and metathesis catalyst for use in a process for producing olefins from a hydrocarbon feed stream, such as a metathesis process for producing propene from a hydrocarbon stream comprising butene. Conversion of 2-butene to propene via utilization of the metathesis and isomerization catalyst is described; however, it should be understood that this is merely for clarity and conciseness and other metathesis reactions are similarly envisioned.

A metathesis reaction is a chemical process involving the exchange of bonds between two reacting chemical species, which results in the creation of products with similar or identical bonding affiliations. This reaction is represented by the general scheme in the following reaction RXN1.

$$A{-}B + C{-}D \rightarrow A{-}D + C{-}B \qquad \text{(RXN1)}$$

As shown in the following reactions RXN2 and RXN3, "isomerization" and "metathesis" of 2-butene to propene is generally a two-step process: 2-butene isomerization using an isomerization catalyst system and then cross-metathesis using a metathesis catalyst system. The 2-Butene Isomerization (reaction RXN2) may be achieved with both the silica and alumina support of the isomerization catalyst and the silica or silica and alumina support of the metathesis and isomerization catalyst. The Cross-Metathesis (RXN3) may be achieved by the oxometallate or metal oxide of the metathesis and isomerization catalyst or the metathesis catalyst. The metathesis and isomerization catalyst provides both the "isomerization" and "metathesis" steps with each component of the isomerization and metathesis catalyst providing individual functionalities.

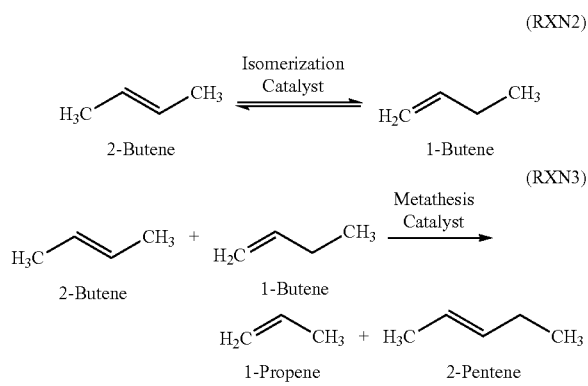

Referring to reactions RXN1 and RXN2, the "isomerization" and "metathesis" reaction is not limited to these reactants and products. However, reactions RXN2 and RXN3 provide a basic illustration of the reaction methodology. As shown in RXN3, the metathesis reaction takes place between two alkenes. The groups bonded to the carbon atoms of the double bond are exchanged between the molecules to produce two new alkenes with the exchanged groups. The specific catalyst that is selected for the olefin metathesis reaction may generally determine whether a cis-isomer or trans-isomer of the olefin reaction products is formed, as the coordination of the olefin molecules with the catalyst play an important role, as do the steric influences of the substituents on the double bond of the newly formed molecule.

Utilizing the aerosol processing system 100 and methods previously discussed in this disclosure for producing metathesis and isomerization catalysts, the metathesis catalysts, or isomerization catalysts may enable control of the properties and characteristics of the catalyst to customize the catalyst for the conversion of a variety of different compounds. Varying the parameters of the aerosol processing method may control formation of the resulting catalysts 101, such as metathesis and isomerization catalyst, metathesis catalyst, or isomerization catalyst for example, to exhibit a range of structural and chemical properties which may be customized or modified for different conversion reactions. For example, adjusting the structural and chemical properties of the catalyst support particles 114 may influence the isomerization functionality of the catalyst 101. Likewise, controlling the rate of condensation of the catalytically active compound precursor vapor 136 onto the catalyst support particles 114, the morphology of catalytically active compound deposited on the surface of the catalyst support particle 114, the amount of catalytically active compound deposited on the surface of the catalyst support particles 114, or both may enable control of the metathesis functionality of the catalyst 101.

The composition of the metathesis and isomerization catalyst, the metathesis catalyst, or the isomerization catalyst may be controlled by changing the catalyst support precursors 104, adding one or a plurality of dopants to the catalyst support precursors 104, modifying relative concentrations of the catalyst support precursors 104 in the catalyst support precursor mixture 108, and changing the type of carrier gas 112. For example, inclusion of a higher relative concentration of one catalyst support precursor, such as the silica precursor or alumina precursor, in the catalyst support precursor mixture 108 will result in a relatively higher concentration of the specific catalyst support precursor in the catalyst support particles 114.

Isomerization reactions are affected by the acidity of the metathesis and isomerization catalyst or the isomerization catalyst. Acidity of the catalyst 101 may be controlled in at least two ways. First, the total number of acidic sites in the catalyst 101 may be controlled by changing the number of aluminum sites in the catalyst support particles 114. The number of aluminum sites may be controlled by modifying the proportion of the alumina precursor in the catalyst support precursor mixture 108 relative to the other precursors. Increasing the aluminum sites present in the catalyst support particles 114 increases the Al—OH that forms in the catalyst 101. Second, the acid strength of each of the aluminum sites is influenced by the environment around each of the aluminum sites and how the aluminum sites interact with the silica sites. The type of catalyst support precursors 104 may have an effect on the formation of aluminum sites. For example, fumed alumina has a large cluster of alumina already formed. Therefore, when fumed alumina is included as the alumina precursor in making silica-alumina based catalyst support particles, the interactions between the alumina and silica are largely predefined and limited to the interface of the two discrete regions of materials. Alternatively, in embodiments in which $Al(NO_3)_3$ is included as the alumina precursor, the aluminum sites created in the catalyst support particles 114 are generally single molecules fully surrounded by silica. Thus, each aluminum site can potentially interact with the silica in all dimensions. In various embodiments, the metathesis and isomerization catalyst, the metathesis catalyst, or the isomerization catalyst formed by the aerosol processing methods may have a total acidity of less than or equal to 0.5 millimole/gram (mmol/g), or from 0.01 mmol/g to 0.5 mmol/g, from 0.1 mmol/g to 0.5 mmol/g, from 0.3 mmol/g to 0.5 mmol/g, or from 0.4 mmol/g to 0.5 mmol/g. It will be appreciated that in further embodiments the metathesis and isomerization catalyst, the metathesis catalyst, or the isomerization catalyst may have a total acidity that is less than 0.01 mmol/g or greater than 0.5 mmol/g. In embodiments, the acidity of the catalyst is sufficient to produce a desired selectivity of propylene and reduced production of undesirable by-products such as aromatics. Increasing acidity may increase the overall butene conversion. However, this increased overall butene conversion may lead to less selectivity and increased production of by-products, such as aromatics for example, which can lead to catalyst coking and deactivation.

The particle size of the metathesis and isomerization catalyst, the metathesis catalyst, or the isomerization catalyst may be controlled by adjusting the concentration of the catalyst support precursor 104 in the catalyst support precursor mixture 108, the type and specification of aerosolizing unit 110, and the reactor configuration. For example, a higher concentration of the catalyst support precursors 104 in the catalyst support precursor mixture 108 relative to water or other diluent 106 results in larger catalyst support particles 114 as less water or other diluent is available to vaporize from each aerosolized droplet. Additionally, different aerosolizing units 110 may produce different size droplets of the aerosolized catalyst support precursor mixture 109 during aerosolization, thus, producing different particle sizes of the catalyst support particles 114. For example, changing the frequency in an ultrasonic nebulizer changes the droplet size of the aerosolized catalyst support precursor mixture 109 generated by the ultrasonic nebulizer. Changing the droplet size changes the particle size of the catalyst support particles 114. Increasing turbulent flow within the aerosolizing unit 110, the first heating zone 120, or both may also increase particle size by causing droplets to collide and coalesce together. Similarly, impactors positioned within the aerosolizing unit 110 or before the first heating zone 120, or both may separate larger wet droplets of the aerosolized catalyst support precursor mixture 109 and permit only smaller droplets to enter and pass through the first heating zone 120. This results in reducing the average size of the catalyst support particles 114. In some embodiments, the catalyst support particles 114 may have a particle size of from 50 nanometers (nm) to 50 microns (μm). In embodiments in which the catalytically active compound precursor forms into clusters or particles that are then deposited on the surfaces of the catalyst support particles 114, the particle size of the catalytically active compound clusters or particles may be less than or equal to 20 nm.

The surface area of the catalyst may be controlled by adjusting the type and amount of the catalyst support precursors 104, including inert constituents, sacrificial constituents, or both, in the catalyst support precursor mixture 108. Inert and sacrificial constituents may include polystyrene latex for example. When heated to high temperatures, the polystyrene latex burns off, leaving pores where the polystyrene latex was previously. One having skill in the art will appreciate that other sacrificial continuants may be utilized which burn off at an elevated temperature to produce a catalyst having an increased surface area caused by removal of the inert and sacrificial constituents from the catalyst. Further, selection of fumed silica and fumed alumina as catalyst support precursors 104 may result in an increased surface area. When aerosolized, the high fractal surface areas of fumed silica and fumed alumina structures are generally preserved. This high fractal surface area results in an increased surface area when compared to non-fumed precursors which result in more spherical, dense particles, with lower surface area since they do not have much internal surface area. The surface area may also be controlled by adjusting the configuration of the aerosol processing system 100. In some embodiments, the catalyst 101 formed by the aerosol processing methods may have a surface area of from 100 meters squared per gram ($m^2/g$) to 700 $m^2/g$. In other embodiments, the catalyst may have a surface area of from 450 $m^2/g$ to 600 $m^2/g$, from 250 $m^2/g$ to 350 $m^2/g$, from 275 $m^2/g$ to 325 $m^2/g$, or from 275 $m^2/g$ to 300 $m^2/g$.

The crystallinity of the catalyst support particles 114 may be controlled by adjusting the type and amount of the catalyst support precursors 104, the temperature of the first heating zone 120, the residence time in the first heating zone 120, and the cooling rate of the catalyst 101. For example, the use of a metal oxide or oxometallate that contains a single metal center versus multiple metal centers as a catalyst support precursor 104 can lead to more dispersion because the fracturing of the cluster is not required. The more metal centers of the metal oxide or oxometallate source that it contains the more fracturing that is required to form crystallinity. Regarding cooling rate, a relatively slower cooling rate provides additional time for the crystal arrangement to occur, where a relatively faster cooling rate can lock atoms into metastable or amorphous states. Regarding temperature and residence time in the first heating zone 120, increasing the temperature, residence time, or both may cause metal oxides or oxometallates to migrate on the surface of the catalyst support particles 114 which may increase crystallite size.

In some embodiments, the catalyst support particles 114 may have a pore size distribution of from 2.5 nanometers (nm) to 40 nm and a total pore volume of at least 0.600 cubic centimeters per gram ($cm^3/g$). Without being bound by theory, the pore size distribution and pore volume are sized to achieve better catalytic activity and reduced blocking of pores by metal oxides, whereas smaller pore volume and pore size catalyst systems are susceptible to pore blocking and thereby reduced catalytic activity. In some embodiments, the catalyst support particles 114 may have a pore size distribution of from 2.5 nm to 40 nm, from 2.5 nm to 20 nm, from 2.5 nm to 4.5 nm, from 2.5 nm to 3.5 nm, from 8 nm to 18 nm, or from 12 nm to 18 nm. In some embodiments, the catalyst may have a total pore volume of from 0.600 $cm^3/g$ to 2.5 $cm^3/g$, from 0.600 $cm^3/g$ to 1.5 $cm^3/g$, from 0.600 $cm^3/g$ to 1.3 $cm^3/g$, from 0.600 $cm^3/g$ to 0.800 $cm^3/g$, from 0.600 $cm^3/g$ to 0.700 $cm^3/g$, or from 0.900 $cm^3/g$ to 1.3 $cm^3/g$.

EXAMPLES

The following examples illustrate the preparation of various metathesis and isomerization catalysts. These metathesis and isomerization catalysts were then used to synthesize propene from a stream of 2-butene and nitrogen in a fixed bed reactor operated at 580° C.

Example 1

Preparation of Metathesis Catalysts Having a Layer of Tungsten Oxide Deposited on the Surface A catalyst support precursor mixture was prepared by adding 37.1 grams of fumed silica to 800 grams of deionized water to produce a catalyst support precursor mixture having 4.5 wt. % fumed silica. The fumed silica used was AEROSIL® 380 fumed silica obtained from Evonik Industries. The catalyst support precursor mixture was sonicated for 20 minutes prior to each experiment. The catalyst support precursor mixture was then aerosolized into a fine mist of micrometer sized droplets using an ultrasonic transducer.

The aerosolized catalyst support precursor mixture was then passed to an aerosol processing system that included a first furnace and a second furnace in series with and downstream of the first furnace. The first furnace (first heating zone) was configured to form agglomerated, spherical particles of fumed silica from the aerosolized catalyst support precursor mixture. The first furnace included a heated length of 12 inches and was maintained at a temperature of 600° C. The second furnace (second heating zone) had a heated length of 6 inches. The overall length of the second furnace was 12 inches, and the heated length of 6 inches extended from a distance of 3 inches from the inlet of the second furnace to a distance of 9 inches from the inlet of the second furnace. The temperature of the second furnace was varied from 600° C. to 1400° C. In particular, experiments were performed at second furnace temperatures of 600° C., 850° C., 1100° C., 1250° C., and 1400° C.

A 1 milliliter (mL) combustion boat containing an initial mass of tungsten oxide ($WO_3$) was positioned in the second furnace at varying positions within the second furnace. The tungsten oxide used was >99% tungsten oxide (lot no. A0348621) obtained from Acros Organics. For temperatures of 600° C., 850° C., and 1100° C., experiments were performed at positions of the combustion boat of WO$_3$ in the second furnace of 3 inches, 6 inches, and 9 inches from the inlet of the second furnace, where the heated zone is located 3 to 9 inches from the inlet of the 12 inch-long tube furnace. For the experiments performed at 1250° C. and 1400° C., a different furnace (24 inch length, capable of reaching the target temperatures) was used as the second furnace, and the combustion boat of WO$_3$ was positioned at the midpoint of the heated zone (12 inches from the inlet of the second furnace). The weight of WO$_3$ in the combustion boat was measured before and after each experiment to determine the amount of WO$_3$ vaporized into the second furnace.

The aerosolized catalyst support precursor mixture was conveyed by a carrier gas through the first furnace and the second furnace at a carrier gas flow rate of 10 liters per minute (L/min) to produce the synthesized metathesis catalysts of Example 1. The carrier gas was particle-free, oil-free air. The synthesized metathesis catalyst was collected on a filter. The amount of WO$_3$ deposited on the synthesized metathesis catalyst was determined by Scanning Electron Microscope and Energy Dispersive Spectroscopy (SEM/EDS). The following Table 1 provides the reaction conditions and amount of WO$_3$ deposited on the surfaces of the synthesized metathesis catalysts.

furnace temperature of 1100° C., the greatest amount of WO$_3$ deposited on the catalyst support particles was 0.484 wt. %, which occurred when the boat was positioned at the midpoint of the heated zone (6 inches from the entrance of the second furnace). At a boat position of 3 inches from the inlet of the second furnace, the amount of WO$_3$ deposited on the catalyst support particles decreased to 0.0684 wt. %, and at a boat position of 9 inches from the entrance of the second furnace, the amount of WO$_3$ deposited on the catalyst support particles also decreased to 0.45 wt. % compared to the amount of WO$_3$ deposited on the catalyst when the boat of WO$_3$ was positioned at the midpoint of the heated zone (6 inches from the inlet of the second furnace). The data for the 1100° C. second furnace temperature illustrates that the position of the source of the catalytically active compound precursor, in this case the WO$_3$, in the second furnace or second heating zone may be used to control the amount of catalytically active compound deposited on the surfaces of the catalyst. Due to this observation, synthesis of the metathesis catalysts at the second furnace temperatures of 1250° C. and at 1400° C. (using a 24 inch long tube furnace) were conducted with the combustion boat of WO$_3$ positioned at the midpoint of the heated section of the second furnace (about 12 inches from the inlet of the 24 inch-long furnace).

TABLE 1

Reaction Conditions and WO$_3$ Content for Synthesis of the Metathesis Catalysts of Example 1.

| Experiment No. | First Furnace Temperature (° C.) | Second Furnace Temperature (° C.) | Residence Time (seconds) | Carrier Gas Flow Rate (L/min) | WO$_3$ Boat Position (inches from inlet) | WO$_3$ Content of Catalyst (wt. %) |
|---|---|---|---|---|---|---|
| 1 | 600 | 600 | 1.0 | 10.0 | 3 | N/A |
| 2 | 600 | 600 | 1.0 | 10.0 | 6 | N/A |
| 3 | 600 | 600 | 1.0 | 10.0 | 9 | <0.0222 |
| 4 | 600 | 850 | 1.0 | 10.0 | 3 | N/A |
| 5 | 600 | 850 | 1.0 | 10.0 | 6 | N/A |
| 6 | 600 | 850 | 1.0 | 10.0 | 9 | 0.0257 |
| 7 | 600 | 1100 | 1.0 | 10.0 | 3 | 0.0684 |
| 8 | 600 | 1100 | 1.0 | 10.0 | 6 | 0.484 |
| 9 | 600 | 1100 | 1.0 | 10.0 | 9 | 0.450 |
| 10 | 600 | 1250 | 1.0 | 10.0 | 12 | 2.54 |
| 11 | 600 | 1400 | 1.0 | 10.0 | 12 | 10.5 |

As shown in Table 1, at temperatures of the second furnace of 600° C. and 850° C., the amounts of WO$_3$ deposited on the surface of the metathesis catalyst were generally not sufficient to allow detection by the SEM/EDS analysis. Measurable amounts of WO$_3$ deposited on the surfaces of the metathesis catalysts in Example 1 were obtained at temperatures in the second furnace of greater than or equal to 850° C. As shown in Table 1, increasing the temperature of the second furnace increased the amount of WO$_3$ deposited on the surfaces of the metathesis catalysts. Thus, it can be concluded from the data in Table 1 that the amount of the WO$_3$ deposited on the surface of the catalyst support particles may be controlled by controlling the temperature of the second furnace (second heating zone 130).

Figure 7:
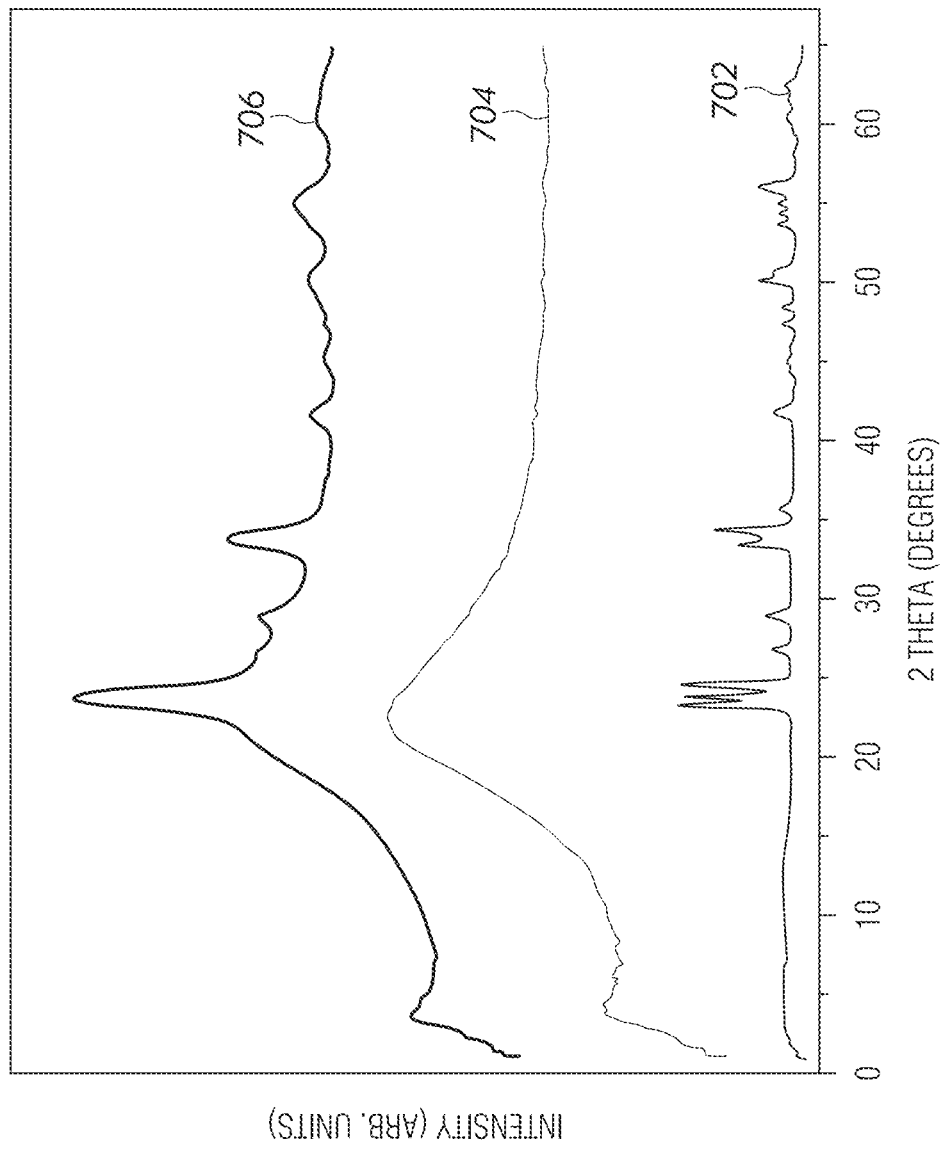
FIG. 7 is a X-Ray Diffraction (XRD) graph illustrating the XRD profiles of metathesis catalysts made by the process of FIG. 1, in accordance with one or more embodiments of the present disclosure.

The amount of the catalytically active compound deposited on the surfaces of the catalyst support particles may also be influenced by the position of the combustion boat of the catalytically active compound precursor within the second heating zone. As shown by the data in Table 1, for the synthesis conducted at a second, 12 inch-long, tube furnace temperature of 1100° C., the amount of WO$_3$ deposited on the catalyst support particles varied with the relative position of the boat of WO$_3$ in the second furnace. At the second The temperature of the second furnace may impact condensation of the WO$_3$ and the ratio of condensation of the WO$_3$ directly onto the surface of the catalyst support particle to self-condensation of the WO$_3$ into clusters or particles that are then deposited onto the surfaces of the catalyst support particles. Referring to FIG. 7, the X-Ray Diffraction (XRD) patterns for the metathesis catalysts synthesized at the second furnace temperatures of 1250° C. and 1400° C. are shown in comparison to the XRD pattern for a tungsten oxide reference 702, which is solid tungsten oxide reference material. The XRD pattern for the metathesis catalyst synthesized at the second furnace temperature of 1250° C. is identified by reference number 704 in FIG. 4. The XRD pattern 704 for the metathesis catalyst synthesized at 1250° C. shows a large single signature peak at about 2θ=22 degrees with no secondary peaks. As previously discussed, the single signature peak at about 2θ=22 degrees is indicative of amorphous material. The lack of secondary peaks indicates the lack of crystallinity in either the catalyst support material or the tungsten oxide deposited on the surfaces of the catalyst support material accessible to vapors and gases. The lack of secondary peaks in the XRD pattern 704 may indicate that the temperature of 1250° C. in the second furnace may result in a preference for condensation of the $WO_3$ vapor directly onto the surface of the catalyst support particles with very little migration of the $WO_3$ during and after condensation. In contrast, the XRD pattern 706 for the metathesis catalyst synthesized at 1400° C. includes several secondary peaks from about 2θ=30° to about 2θ=60°. These secondary peaks may indicate some degree of crystallinity of the $WO_3$, which may result from self-condensation of the $WO_3$ into particles or clusters before depositing on the surface of the catalyst support particles or migration of $WO_3$ that has condensed directly onto the surface of the catalyst support particles. This demonstrates that the mechanism for depositing the catalytically active compound onto the catalyst support particle may be controlled by increasing or decreasing the temperature of the second heating zone 130 (e.g., controlling the temperature of the second furnace). The presence of secondary peaks in the XRD pattern 706 may also indicate higher loading of $WO_3$ resulting from increased vaporization of the $WO_3$ in the second furnace at the higher temperature of 1400° C. At the higher $WO_3$ loading for 1400° C. (greater than 10%), there are more crystalline species of $WO_3$. Thus, the temperature of the second furnace (second heating zone) may be used to control the amount of $WO_3$ vaporized in the second furnace to control the amount of crystalline $WO_3$ deposited on the surface of the catalyst support particles.

Comparative Example 2

Metathesis Catalyst Prepared by Wet Impregnation of $WO_3$ onto a Silica Support A conventional metathesis catalyst prepared by wet impregnating $WO_3$ onto a silica support was provided for comparison to the metathesis catalysts of Example 1. The silica support was CARiACT Q-10 silica catalyst support obtained from Fuji Silysia Chemical. The silica catalyst support was wet impregnated with a solution of ammonium metatungstate hydrate to produce the catalyst of Comparative Example 2 having 10 wt. % $WO_3$ based on the total weight of the catalyst. A catalyst support precursor mixture was prepared by adding 37.7 grams fumed silica to 800 grams of deionized water to produce a catalyst support precursor mixture having 4.5 wt. % fumed silica. The catalyst support precursor mixture was aerosolized using an ultrasonic transducer and introduced to the aerosol processing system described in Example 1. The combustion boat of $WO_3$ was not present in the second furnace. The aerosolized catalyst support precursor mixture was transferred to a heated furnace at 1400° C. with a flow of air at 5 L/min. Flow of air was continued for 120 min. Upon exit from the heated furnace, the formed metathesis and isomerization catalyst was collected in a filter. The resulting catalyst support particles were substantially free of $WO_3$.

The catalyst support particles were then wet impregnated with $WO_3$ by adding 0.220 grams of the catalyst support particles collected in the filter to 0.023 grams of ammonium metatungstate and 2 ml of water in a 2 dram vial. The vial was rolled at 15 rotations per minute (rpm) for 2 hours. Subsequently, the solution was heated at atmospheric pressure and a temperature of 85° C. for 16 hours (h) to dry. The resulting catalyst support particles having the wet impregnated ammonium metatungstate was then calcined in a furnace at 550° C. for 480 min to produce the metathesis catalyst wet impregnated with $WO_3$.

Example 3

Evaluation of the Performance of the Metathesis Catalysts of Example 1 and Comparative Example 2 for Metathesizing Butene to Produce Propene The metathesis catalysts of Example 1 and Comparative Example 2 were evaluated for their performance in metathesizing 2-butene to propene. The performance of each of the example metathesis catalysts were tested in a fixed bed reactor for conversion of a stream of 2-butene to propene. The fixed-bed flow reactor system had a quartz tube with a bed of metathesis and isomerization catalyst disposed between layers of quartz wool. Each of the metathesis catalysts to be tested was serially mounted in the quartz tube as the bed of metathesis and isomerization catalyst disposed between the layers of quartz wool. Each metathesis catalyst was tested sequentially to provide performance data for each metathesis catalyst. Each metathesis catalyst was first activated at 580° C. under nitrogen flow at 0.005 liters/minute (L/min) for 1 hour. At the desired reaction temperature (580° C.), a feed stream comprising trans-2-butene was introduced into the reactor to start the reaction. The reaction was performed at 550° C. and at a gas hourly space velocity of 900 per hour ($h^{-1}$), using nitrogen as a diluent. The feed stream had 10 wt. % trans-2-butene based on the total mass flow rate of the feed stream. The flow stream exiting the fixed bed flow reactor was passed to a gas chromatograph for analysis of the product stream. The percentage of propene selectivity for each of the metathesis catalysts in Example 1 and Comparative Example 2 are provided subsequently in Table 2. Table 2 also provides the amount of $WO_3$ in each of the metathesis catalysts.

TABLE 2

Propene yield and amount of $WO_3$ on the catalysts of Example 1 and Comparative Example 2

| Example | Experiment No. | Method of Applying $WO_3$ | Amount of $WO_3$ (wt. %) | Propene Yield (%) |
|---|---|---|---|---|
| 1 | 1 | Aerosol Process | N/A | N/A |
| 1 | 2 | Aerosol Process | N/A | N/A |
| 1 | 3 | Aerosol Process | <0.0222 | N/A |
| 1 | 4 | Aerosol Process | N/A | N/A |
| 1 | 5 | Aerosol Process | N/A | N/A |
| 1 | 6 | Aerosol Process | 0.0257 | N/A |
| 1 | 7 | Aerosol Process | 0.0684 | 15.65 |
| 1 | 8 | Aerosol Process | 0.484 | 27.63 |
| 1 | 9 | Aerosol Process | 0.450 | 25.60 |
| 1 | 10 | Aerosol Process | 2.54 | 37.20 |
| 1 | 11 | Aerosol Process | 10.5 | 34.17 |
| Comparative Ex. 2 | 1 | Wet Impregnation | 10 | 33.63 |

As shown in Table 2, the metathesis catalysts of Example 1 synthesized at second furnace temperatures of greater than 850° C. provided unexpectedly high performance. As previously discussed in this disclosure, for an isomerization and metathesis catalyst, the silica-alumina of the catalyst support particle may contribute primarily to isomerization, while the metathesis functionality is primarily provided by the metal oxide, such as $WO_3$. Thus, it is expected that increasing the $WO_3$ would increase the metathesis functionality of the catalyst and improve the yield of propene from metathesis of butene. However, it was unexpectedly found that the catalyst of Experiment 10 of Example 1 having only 2.54 wt. % $WO_3$ performed the best with a propene yield of 37.20%. The catalyst of Experiment 10 of Example 1 was synthesized using the aerosol processing system described in Example 1 with the temperature of the second furnace set to 1250° C. This propene yield of 37.20% obtained using the catalyst of Experiment 10 of Example 1 was an 11% improvement over the propene yield of 33.63% obtained using the catalyst of Comparative Example 2 having 10 wt. % $WO_3$ and prepared using wet impregnation. This result was unexpected because the catalyst of Experiment 10 of Example 1 had only 2.54 wt. % $WO_3$, which was only 25% of the $WO_3$ content of the catalyst of Comparative Example 2, which had 10 wt. % $WO_3$. Thus, it has been shown that the aerosol processing systems and method described in this disclosure can be used to produce a metathesis catalyst having superior propene yield performance and a lesser amount of catalytically active compound compared to conventional metathesis catalysts prepared by wet impregnation and having 10 wt. % or more of the catalytically active compound.

It was also observed that the catalyst generated from Experiment 11 of Example 1 at a second furnace temperature of 1400° C., which had a $WO_3$ content of 10.5 wt. %, did not perform as well as the catalyst generated from Experiment 10 of Example 1 at a second furnace temperature of 1250° C., which had a $WO_3$ content of 2.54 wt. %. The catalyst of Experiment 11 of Example 1 resulted in a propene yield of 34.17%, which was 8% less than the propene yield of 37.20% obtained using the catalyst of Experiment 10 of Example 1. This observation may be attributed to a higher degree of crystallization of the $WO_3$ on the surface of the catalyst of Experiment 11 of Example 1. The crystalline $WO_3$ is known to be less active for the metathesis reaction. Referring to FIG. 7, as previously discussed in Example 1, the XRD pattern 706 for the catalyst of Experiment 11 produced at the second furnace temperature of 1400° C. exhibited a greater degree of crystallinity as shown by the number and magnitude of the secondary peaks compared to the XRD pattern 704 for the catalyst of Experiment 10 produced at the second furnace temperature of 1250° C., which exhibited little or no secondary peaks. Comparing the XRD pattern 706 of the catalyst of Experiment 11 with the XRD pattern 702 of the $WO_3$ reference standard it was observed that both XRD pattern 702 and XRD pattern 706 exhibited multiple secondary peaks between about $2\theta=30°$ and $2\theta=60°$, which were representative of crystallinity in the $WO_3$. Increasing crystallinity in the $WO_3$ decreases the catalytic activity of the $WO_3$, thus, reducing the propene yield. Example 3 demonstrated that increasing the temperature in the second furnace (second heating zone 130) may enable control of the amount of $WO_3$ deposited on the surfaces of the catalyst support particles, the mechanism of depositing the $WO_3$ on the surfaces of the catalyst support particles, or both to control the catalytic activity of the catalyst.

Example 4

Evaluation of the Degree of to which the Catalytically Active Compound is Dispersed on the Surface of the Catalyst The metathesis catalyst of Experiment 10 of Example 1 and the wet impregnation metathesis catalyst of Comparative Example 2 were analyzed using X-ray Diffraction to evaluate the degree to which the catalytically active compound was dispersed on the outer surface of the catalyst. Referring to FIG. 8, the XRD pattern 804 is shown for the metathesis catalyst of Experiment 10 of Example 1 having tungsten oxide as the catalytically active compound deposited onto the catalyst support particle 114 by the aerosol processing method described in Example 1. The XRD pattern 804 for the catalyst of Experiment 10 of Example 1 exhibited a single signature peak 820 at about $2\theta=22$ degrees indicative of amorphous materials in the catalyst 101. The XRD pattern 804 for the metathesis catalyst of Experiment 10 of Example 1 did not exhibit secondary peaks above $2\theta=30$ degrees, and thus, does not exhibit a measurable degree of crystallinity of the tungsten oxide or the catalyst support particle. FIG. 8 also shows the XRD pattern for the metathesis catalyst of Comparative Example 2 prepared by wet impregnation. As shown in FIG. 8, the XRD pattern 802 for the conventional wet impregnated catalyst exhibits a background peak with a major peak 806 at about $2\theta=22$ degrees and several secondary peaks 808, 810, 812, and 814 from about $2\theta=30°$ to about $2\theta=60°$. As previously described, the peaks 806, 808, 810, 812, and 814 in the XRD pattern 802 indicate a measurable degree of crystallinity of the tungsten oxide on the surface of the metathesis catalyst of Comparative Example 2 prepared by conventional wet impregnation methods. The additional crystallinity indicates that the tungsten oxide applied using wet impregnation formed clusters and crystals on the surface of the catalyst support particle 114, thus decreasing the degree to which the tungsten oxide was dispersed on the surface of the metathesis catalyst of Comparative Example 2 compared to the metathesis catalyst of Experiment 10 of Example 1. The XRD pattern 804 for the metathesis catalyst of Experiment 10 of Example 1 did not exhibit secondary peaks, which indicates that the metathesis catalyst of Experiment 10 of Example 1 does not have a measurable degree of crystallinity of the tungsten oxide compared to the metathesis catalyst of Comparative Example 2.

Figure 9:
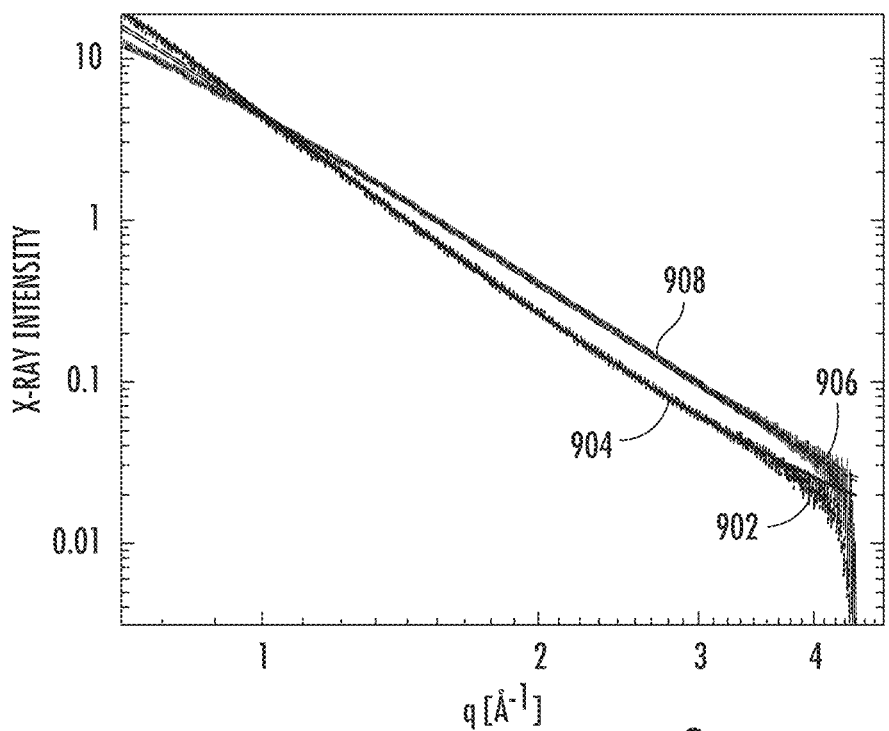
FIG. 9 is an azimuthally averaged Small Angle X-Ray Scattering (SAXS) spectra of the metathesis catalyst made by the process of FIG. 1, in accordance with one or more embodiments of the present disclosure, compared to the SAXS spectra of a metathesis catalyst made by conventional wet impregnation processes.

The catalyst of Experiment 10 of Example 1 and the catalyst of Comparative Example 2 were then evaluated for average particle size according to the SAXS method previously described in this disclosure. The SAXS spectra generated from the SAXS method and lognormal models fit to the spectra data are provided in FIG. 9. Reference number 902 represents the SAXS spectra data for the catalyst of Comparative Example 2 and reference number 904 indicates the lognormal fit to the spectra data for the catalyst of Comparative Example 2. Reference number 906 represents the SAXS spectra data for the catalyst of Experiment 10 of Example 1 and reference number 904 indicates the lognormal fit to the spectra data for the catalyst of Experiment 10 of Example 1.

The catalyst of Comparative Example 2, which was produced by wet impregnation, exhibited tungsten oxide clusters having an average particle radius of from 44.8 angstroms (4.48 nm) to 46.4 angstroms (4.64 nm). In comparison, the catalyst of Experiment 10 of Example 1, which was produced using the aerosol processing method described in Example 1, exhibited tungsten oxide an average particle radius of from 3.8 angstroms (0.38 nm) to 4.4 angstroms (0.44 nm). As shown by these measurements, the average particle size of the tungsten oxide deposited on the surface of the catalyst of Experiment 10 of Example 1 was substantially less than the average particle size of the tungsten oxide deposited on the surface of the catalyst of Example 2. The smaller particle size of the tungsten oxide deposited on the catalyst of Experiment 10 of Example 1 shows that the tungsten oxide is more dispersed over the outer surface of the catalyst particle compared to the tungsten oxide deposited on the catalyst of Comparative Example 2. Thus, the aerosol processing methods of the present disclosure may result in the catalytically active compound being more dispersed over the surface of the catalyst support compared to conventional wet impregnation methods.

A first aspect of the present disclosure may be directed to a method of producing a catalyst, the method comprising: generating an aerosolized flow of catalyst support particles; heating a catalytically active compound precursor to produce a catalytically active compound precursor vapor; contacting the aerosolized flow of catalyst support particles with the catalytically active compound precursor vapor; and condensing the catalytically active compound precursor to produce the catalyst comprising a catalytically active compound deposited on surfaces of the catalyst support particles.

A second aspect of the present disclosure may include the first aspect where the catalyst support particles comprise at least one of silica, alumina, or silica-alumina.

A third aspect of the present disclosure may include the first or the second aspect where the catalytically active compound precursor comprises at least one of tungsten, platinum, gold, palladium, rhodium, iridium, chromium, rhenium, molybdenum, manganese, titanium, cerium, or combinations of these.

A fourth aspect of the present disclosure may include any of the first through third aspects where the catalytically active compound precursor comprises at least one of tungsten metal, tungsten (IV) oxide, tungsten (VI) oxide, ammonium metatungstate hydrate, tungstic acid, or sodium tungstate.

A fifth aspect of the present disclosure may include any of the first through third aspects where the catalytically active compound precursor comprises a tungsten-containing compound that vaporizes or decomposes into a vapor at a temperature of from 150° C. to 1500° C.

A sixth aspect of the present disclosure may include any of the first through fifth aspects where the aerosolized flow of catalyst support particles is contacted with the catalytically active compound precursor vapor at a temperature of from 600° C. to 1450° C.

A seventh aspect of the present disclosure may include any of the first through sixth aspects comprising contacting the aerosolized flow of catalyst support particles with the catalytically active compound precursor vapor at ambient pressure and cooling the aerosolized flow of catalyst support particles and the catalytically active compound precursor vapor to a temperature of less than 120° C.

An eighth aspect of the present disclosure may include any of the first through seventh aspects where the catalytically active compound precursor vapor condenses directly onto the surfaces of the catalyst support particles.

A ninth aspect of the present disclosure may include any of the first through seventh aspects where the catalytically active compound precursor vapor nucleates and condenses to form clusters, particles, or both and the clusters, particles, or both deposit onto the surfaces of the catalyst support particles.

A tenth aspect of the present disclosure may include any of the first through ninth aspects where the catalyst comprises from 0.02 wt. % to 20 wt. % catalytically active compound.

An eleventh aspect of the present disclosure may include any of the first through tenth aspects where an interior of the catalyst support particles is substantially free of the catalytically active compound.

A twelfth aspect of the present disclosure may include any of the first through eleventh aspects where generating an aerosolized flow of catalyst support particles comprises: aerosolizing a catalyst support precursor mixture comprising a catalyst support precursor and a diluent; and drying the aerosolized catalyst support precursor mixture to produce the aerosolized flow of catalyst support particles.

A thirteenth aspect of the present disclosure may include the twelfth aspect where the catalyst support precursor comprises at least one of silica, fumed silica, alumina, fumed alumina, or alumina-silica and the diluent comprises water, an organic solvent, or a combination of these.

A fourteenth aspect of the present disclosure may include the twelfth or thirteenth aspects where the catalyst support precursor mixture comprises from 1 weight percent (wt. %) to 20 wt. % catalyst support precursor, based on the total weight of the catalyst support precursor mixture.

A fifteenth aspect of the present disclosure may include any of the twelfth through fourteenth aspects where the aerosolized catalyst support precursor mixture is dried at a temperature of from 200° C. to 1450° C.

A sixteenth aspect of the present disclosure may include a method of producing a catalyst, the method comprising: aerosolizing a catalyst support precursor mixture comprising a catalyst support precursor and a diluent to produce an aerosolized catalyst support precursor mixture; passing the aerosolized catalyst support precursor mixture to a first heating zone; drying the aerosolized catalyst support precursor mixture in the first heating zone to form a plurality of aerosolized catalyst support particles; passing the plurality of aerosolized catalyst support particles to a second heating zone downstream of the first heating zone; contacting the plurality of aerosolized catalyst support particles with a catalytically active compound precursor vapor in the second heating zone; and condensing the catalytically active compound precursor vapor to produce the catalyst comprising a catalytically active compound deposited on surfaces of the catalyst support particles.

A seventeenth aspect of the present disclosure may include the sixteenth aspect where the catalyst support precursor comprises at least one of silica, fumed silica, alumina, fumed alumina, or alumina-silica and the diluent comprises water, an organic solvent, or a combination of these.

An eighteenth aspect of the present disclosure may include the sixteenth or seventeenth aspects where the catalyst comprises from 0.02 wt. % to 20 wt. % catalytically active compound.

A nineteenth aspect of the present disclosure may include any of the sixteenth through eighteenth aspects where an interior of the catalyst support particles is substantially free of the catalytically active compound.

A twentieth aspect of the present disclosure may include any of the sixteenth through nineteenth aspects where the catalytically active compound precursor vapor comprises at least one of tungsten metal, tungsten (IV) oxide, tungsten (VI) oxide, ammonium metatungstate hydrate, tungstic acid, or sodium tungstate.

A twenty-first aspect of the present disclosure may include any of the sixteenth through twentieth aspects where the first heating zone is maintained at a temperature of from 200° C. to 1450° C.

A twenty-second aspect of the present disclosure may include any of the sixteenth through twenty-first aspects where the aerosolized flow of catalyst support particles is contacted with the catalytically active compound precursor vapor in the second heating zone at a temperature of from 600° C. to 1450° C.

A twenty-third aspect of the present disclosure may include any of the sixteenth through twenty-second aspects comprising cooling the aerosolized flow of catalyst support particles and the catalytically active compound precursor vapor at a controlled rate to a temperature from 20° C. to 120° C. downstream of the second heating zone.

A twenty-fourth aspect of the present disclosure may include any of the sixteenth through twenty-third aspects further comprising vaporizing a catalytically active compound precursor to form the catalytically active compound precursor vapor.

A twenty-fifth aspect of the present disclosure may include the twenty-fourth aspect comprising heating the catalytically active compound precursor in a crucible in the second heating zone to vaporize the catalytically active compound precursor into the catalytically active compound precursor vapor.

A twenty-sixth aspect of the present disclosure may include twenty-fourth or twenty-fifth aspects where the temperature of the catalytically active compound precursor in the second heating zone is from 50° C. to 2000° C.

A twenty-seventh aspect of the present disclosure may include the twenty-fourth aspect comprising heating the catalytically active compound precursor in a third heating zone to produce the catalytically active compound precursor vapor and passing the catalytically active compound precursor vapor to the second heating zone.

A twenty-eighth aspect of the present disclosure may include any of the sixteenth through twenty-seventh aspects where the second heating zone comprises a reaction tube extending through a second furnace and where the method further comprises seasoning the reaction tube extending through the second furnace with the catalytically active compound precursor.

A twenty-ninth aspect of the present disclosure may include the twenty-eighth aspect where seasoning the reaction tube comprises: heating the catalytically active compound precursor to form a catalytically active compound precursor vapor; and condensing the catalytically active compound precursor vapor onto an inner surface of the reaction tube to form a layer of the catalytically active compound precursor on the inner surface of the reaction tube.

A thirtieth aspect of the present disclosure may include the twenty-ninth aspect further comprising: heating the reaction tube to re-vaporize the catalytically active compound precursor from the inner surface of the reaction tube to produce the catalytically active compound precursor vapor; passing the plurality of catalyst support particles through the reaction tube where the plurality of catalyst support particles contact the catalytically active compound precursor vapor; and condensing the catalytically active compound precursor vapor on a surface of the plurality of catalyst support particles.

A thirty-first aspect of the present disclosure may include a catalyst made by the method in any of the sixteenth through thirtieth aspects.

A thirty-second aspect of the present disclosure may be directed to a catalyst prepared by the a process comprising: generating an aerosolized flow of catalyst support particles; heating a catalytically active compound precursor to produce a catalytically active compound precursor vapor; contacting the aerosolized flow of catalyst support particles with the catalytically active compound precursor vapor; and condensing the catalytically active compound precursor to produce the catalyst comprising a catalytically active compound deposited on surfaces of the catalyst support particles.

A thirty-third aspect of the present disclosure may include the thirty-second aspect where the catalytically active compound is condensed directly onto the surfaces of the plurality of catalyst support particles.

A thirty-fourth aspect of the present disclosure may include the thirty-second aspect where the catalytically active compound comprises clusters, particles, or both of the catalytically active compound deposited on the surfaces of the plurality of catalyst support particles.

A thirty-fifth aspect of the present disclosure may include any of the thirty-second through thirty-fourth aspects where the catalytically active compound precursor comprises at least one of tungsten, platinum, gold, palladium, rhodium, iridium, chromium, rhenium, molybdenum, manganese, titanium, cerium, or combinations of these.

A thirty-sixth aspect of the present disclosure may include any of the thirty-second through thirty-fifth aspects where the catalytically active compound precursor is at least one of tungsten metal, tungsten (IV) oxide, tungsten (VI) oxide, ammonium metatungstate hydrate, tungstic acid, or sodium tungstate.

A thirty-seventh aspect of the present disclosure may include any of the thirty-second through thirty-sixth aspects where the process comprises contacting the aerosolized flow of catalyst support particles with the catalytically active compound precursor vapor at ambient pressure and cooling the aerosolized flow of catalyst support particles and the catalytically active compound precursor vapor to a temperature of less than 120° C.

A thirty-eighth aspect of the present disclosure may include any of the thirty-second through thirty-seventh aspects where generating an aerosolized flow of catalyst support particles comprises: aerosolizing a catalyst support precursor mixture comprising a catalyst support precursor and a diluent; and drying the aerosolized catalyst support precursor mixture to produce the aerosolized flow of catalyst support particles.

A thirty-ninth aspect of the present disclosure may include any of the thirty-second through thirty-eighth aspects where the aerosolized flow of catalyst support particles is contacted with the catalytically active compound precursor vapor at a temperature of from 600° C. to 1450° C.

A fortieth aspect of the present disclosure may include any of the thirty-second through thirty-ninth aspects comprising from 0.02 wt. % to 20 wt. % catalytically active compound based on the total weight of the catalyst.

A forty-first aspect of the present disclosure may include any of the thirty-second through fortieth aspects where an interior of the catalyst support particles is substantially free of the catalytically active compound.

A forty-second aspect of the present disclosure may be directed to a catalyst comprising: a plurality of catalyst support particles comprising silica, alumina, or silica and alumina; and a catalytically active compound deposited onto surfaces of a plurality of catalyst support particles, the surfaces of the plurality of catalyst support particles being accessible to gases and vapors, where the catalytically active compound comprises tungsten.

A forty-third aspect of the present disclosure may include the forty-second aspect where the catalytically active compound is condensed directly onto the surfaces of the plurality of catalyst support particles.

A forty-fourth aspect of the present disclosure may include the forty-second or forty-third aspects where the catalytically active compound comprises at least one of single atoms, single molecules, clusters, particles, or combinations of these of the catalytically active compound deposited on the surfaces of the plurality of catalyst support particles.

A forty-fifth aspect of the present disclosure may include the forty-second through forty-fourth aspects comprising from 0.02 wt. % to 20 wt. % catalytically active compound based on the total weight of the catalyst.

A forty-sixth aspect of the present disclosure may include the forty-second through forty-fifth aspects where an interior of the catalyst support particles is substantially free of the catalytically active compound.

A forty-seventh aspect of the present disclosure may include the forty-second through forty-sixth aspects where the catalytically active compound deposited onto surfaces of the plurality of catalyst support particles has an average crystalline size of less than 2.5 nanometers, where the average crystalline size is an average radius of particles of the catalytically active compound determined using Small Angle X-Ray Scattering (SAXS).

A forty-eighth aspect of the present disclosure may include the forty-second through forty-seventh aspects where the catalyst has an X-Ray Diffraction pattern consisting of a single signature peak within a range of from 2 theta greater than or equal to 15 degrees to 2 theta less than or equal to 60 degrees.

A forty-ninth aspect of the present disclosure may be directed to a system for producing a catalyst, the system comprising: an aerosolizing unit; a first heating zone downstream of the aerosolizing unit; a second heating zone downstream of the first heating zone, the second heating zone comprising an inlet configured to introduce a catalytically active compound precursor to the second mixing zone; where an aerosolized catalyst support precursor mixture is configured to be aerosolized by the aerosolizing unit and flows through the first heating zone and then the second heating zone.

A fiftieth aspect of the present disclosure may include the forty-ninth aspect where the aerosolizing unit comprises an ultrasonic transducer, a spray nozzle, or an ultrasonic transducer and a spray nozzle.

A fifty-first aspect of the present disclosure may include the forty-ninth through fiftieth aspects where the aerosolizing unit is an ultrasonic transducer.

A fifty-second aspect of the present disclosure may include any of the forty-ninth through fifty-first aspects further comprising a crucible disposed within the second heating zone and configured to contain and expose the catalytically active compound precursor to the second heating zone.

A fifty-third aspect of the present disclosure may include any of the forty-ninth through fifty-second aspects further comprising a first furnace and a second furnace, where the first heating zone is disposed within the first furnace and the second heating zone is disposed within the second furnace.

A fifty-fourth aspect of the present disclosure may include the fifty-third aspect further comprising a reaction tube extending from the aerosolizing unit through the first furnace and through the second furnace.

A fifty-fifth aspect of the present disclosure may include the fifty-fourth aspect where the first heating zone comprises a first portion of the reaction tube positioned within the first furnace and the second heating zone comprises a second portion of the reaction tube positioned within the second furnace.

A fifty-sixth aspect of the present disclosure may include the fifty fourth aspect where the source of the catalytically active compound precursor vapor comprises a layer of a catalytically active compound precursor deposited on an inner surface of a portion of the reaction tube disposed within the first furnace, the second furnace, or both the first furnace and the second furnace.

A fifty-seventh aspect of the present disclosure may include any of the forty-ninth through fifty-second aspects where the second heating zone comprises a reaction tube and the source of the catalytically active compound precursor vapor comprises a layer of the catalytically active compound precursor condensed on an inner surface of a portion of the reaction tube.

A fifty-eighth aspect of the present disclosure may include any of the forty-ninth through fifty-seventh aspects further comprising a filter downstream of the second heating zone.

A fifty-ninth aspect of the present disclosure may include any of the forty-ninth through fifty-eighth aspects where the aerosolizing unit comprises a carrier gas inlet to supply a carrier gas to convey the aerosolized catalyst support precursor mixture from the atomizer, through the first heating zone, and through the second heating zone and into the separator.

It should now be understood that various aspects of the systems and methods of making catalytic materials via aerosol processing are described and such aspects may be utilized in conjunction with various other aspects.

Throughout this disclosure ranges are provided for various processing parameters and characteristics of the metathesis and isomerization catalyst, metathesis catalyst, or isomerization catalyst. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus it is intended that the specification cover the modifications and variations of the various described embodiments provided such modifications and variations come within the scope of the appended claims and their equivalents.

What is claimed is:

1. A method of producing a catalyst, the method comprising:
   aerosolizing a catalyst support precursor mixture comprising a catalyst support precursor and a diluent;
   drying the aerosolized catalyst support precursor mixture to produce an aerosolized flow of catalyst support particles;
   heating a catalytically active compound precursor to produce a catalytically active compound precursor vapor;
   contacting the aerosolized flow of catalyst support particles with the catalytically active compound precursor vapor; and
   condensing the catalytically active compound precursor to produce the catalyst comprising a catalytically active compound deposited on surfaces of the catalyst support particles.

2. The method of claim 1 where the catalyst support particles comprise at least one of silica, alumina, or silica-alumina.

3. The method of claim 1 where the catalytically active compound precursor comprises at least one of tungsten, platinum, gold, palladium, rhodium, iridium, chromium, rhenium, molybdenum, manganese, titanium, cerium, or combinations of these.

4. The method of claim 1 where the catalytically active compound precursor comprises a tungsten-containing compound that vaporizes or decomposes into a vapor at a temperature of from 150° C. to 1500° C.

5. The method of claim 1 where the aerosolized flow of catalyst support particles is contacted with the catalytically active compound precursor vapor at a temperature of from 600° C. to 1450° C.

6. The method of claim 1 comprising contacting the aerosolized flow of catalyst support particles with the catalytically active compound precursor vapor at ambient pressure and cooling the aerosolized flow of catalyst support particles and the catalytically active compound precursor vapor to a temperature of less than 120° C.

7. The method of claim 1 where the catalytically active compound precursor vapor condenses directly onto the surfaces of the catalyst support particles.

8. The method of claim 1 where the catalytically active compound precursor vapor nucleates and condenses to form clusters, particles, or both and the clusters, particles, or both deposit onto the surfaces of the catalyst support particles.

9. The method of claim 1 where the catalyst comprises from 0.02 wt. % to 20 wt. % catalytically active compound.

10. The method of claim 1 where the catalyst support precursor comprises at least one of silica, fumed silica, alumina, fumed alumina, or alumina-silica and the diluent comprises water, an organic solvent, or a combination of these.

11. The method of claim 10 where the catalyst support precursor mixture comprises from 1 weight percent (wt. %) to 20 wt. % catalyst support precursor, based on the total weight of the catalyst support precursor mixture.

12. The method of claim 10 where the aerosolized catalyst support precursor mixture is dried at a temperature of from 200° C. to 1450° C.

* * * * *

UNITED STATES PATENT AND TRADEMARK OFFICE
CERTIFICATE OF CORRECTION

PATENT NO. : 10,780,421 B2
APPLICATION NO. : 15/998699
DATED : September 22, 2020
INVENTOR(S) : Maxim Bukhovko and Michele Louisa Ostraat Page 1 of 1

It is certified that error appears in the above-identified patent and that said Letters Patent is hereby corrected as shown below:

In the Specification

Column 6, Line 7, delete "then then" and insert --then--, therefor.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*